United States Patent [19]

Watanabe et al.

[11] Patent Number: 5,232,924
[45] Date of Patent: Aug. 3, 1993

[54] HETEROCYCLIC COMPOUND HAVING SEROTONINE 2-RECEPTOR ANTAGONISTIC ACTIVITY

[75] Inventors: Yoshifumi Watanabe; Hiroyuki Usui; Toshiro Shibano; Tsuyoshi Tanaka; Yoshiyuki Morishima; Megumi Yasuoka, all of Tokyo, Japan

[73] Assignee: Daiichi Pharmaceutical Co., Ltd., Tokyo, Japan

[21] Appl. No.: 533,644

[22] Filed: Jun. 5, 1990

[30] Foreign Application Priority Data

| Jun. 5, 1989 [JP] | Japan | 1-142397 |
| Jul. 20, 1989 [JP] | Japan | 1-188617 |
| Aug. 3, 1989 [JP] | Japan | 1-202039 |
| Nov. 29, 1989 [JP] | Japan | 1-310346 |

[51] Int. Cl.$^5$ .................... A61K 43/64; C07D 487/04
[52] U.S. Cl. ................................ 514/246; 544/223
[58] Field of Search ........................ 544/223, 246

[56] References Cited

U.S. PATENT DOCUMENTS

3,609,148  9/1971  Hoegerle ........................ 260/248

FOREIGN PATENT DOCUMENTS

| 0062873 | 10/1982 | European Pat. Off. . |
| 0069953 | 1/1983 | European Pat. Off. . |
| 0081584 | 6/1983 | European Pat. Off. . |
| 1922837 | 11/1969 | Fed. Rep. of Germany . |
| 1328205 | 8/1973 | United Kingdom . |

OTHER PUBLICATIONS

"The Journal of Organic Chemistry", vol. 43, No. 25, 1978 Prisbe, E. J.; Verheyden, J. P. H.; Moffatt, J. G.

*Primary Examiner*—Robert W. Ramsuer
*Attorney, Agent, or Firm*—Sughrue, Mion, Zinn, Macpeak & Seas

[57] ABSTRACT

A heterocyclic compound represented by formula (I):

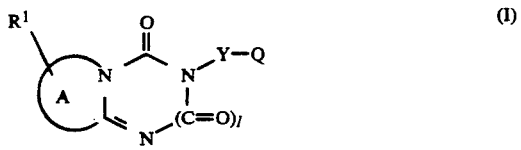

wherein $R^1$ represents a hydrogen atom, an alkyl group, an aryl group which may be substituted with one or more substituents selected from the group consisting of a halogen atom, an alkoxy group, an alkyl group and a trihalogenomethyl group; $\lambda$ represents 0 or 1; ring A represents a 6 membered heterocyclic ring containing the nitrogen atom shared with the triazine ring and which may contain one or more double bonds; Y represents a substituted or unsubstituted alkylene group having 1 to 15 carbon atoms; and Q represents a group represented by formula (II):

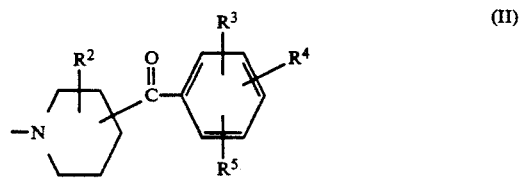

wherein $R^2$, $R^3$, $R^4$ and $R^5$ are represented by substituents disclosed herein; or salt thereof, and intermediates therefor are described.

The compound of formula (I) or salt thereof exhibit selective serotonin 2-receptor antagonistic activity and are useful for the prevention or treatment of circulatory diseases, e.g., ischemic heart diseases, cerebral vessel disturbances, and peripheral circulation disturbances.

9 Claims, No Drawings

HETEROCYCLIC COMPOUND HAVING SEROTONINE 2-RECEPTOR ANTAGONISTIC ACTIVITY

FIELD OF THE INVENTION

This invention relates to a heterocyclic compound represented by formula (I) shown below, salts thereof, and intermediates therefor. Also, this invention relates to a serotonin 2-receptor antagonist and a preventing or treating agent for heart diseases, which contains the compound of formula I) or salts thereof as an active ingredient. The heterocyclic compound of formula (I) and salts thereof exhibit selective serotonin 2-receptor antagonistic activity and are useful for the prevention and treatment of circulatory diseases, e.g., ischemic heart diseases such as angina pectoris, myocardial infarction, heart failure, restenosis after percutaneous transluminal coronary angioplasty, cerebral vessel disturbances such as cerebral infarction, brain injury after subarachnoidal hemorrhage, and peripheral circulation disturbances such as Raynaud disease, Buerger disease.

BACKGROUND OF THE INVENTION

Known treating agents for heart diseases, e.g., angina pectoris, myocardial infarction, and heart failure, include β-blockers, calcium blockers, and cardiotonics.

Drugs having serotonin 2-receptor antagonistic activity have recently been studied as treating agents for the heart diseases, but there has been found no drug having sufficient effects.

Serotonin has strong physiological activities, such as blood platelet aggregation and vasoconstriction, and is a neurotransmitter. Serotonin is known to act serotonin receptors, and the serotonin receptors are known to include serotonin 1-receptor, serotonin 2-receptor, etc. In case of cardiac infarction endothelial cells of coronary vessels are injured and in such case it is considered that serotonin causes vasoconstriction or thrombus formation through serotonin 2-receptor, resulting in further reduction of blood supply to the ischemic site of the myocardium. From this point of view, drugs for treating ischemic heart diseases have also been studied.

As a representative serotonin 2-receptor antagonist which has been clinically used, Ketanserin is known. Also, Ritanserin and Irindalone are known as serotonin 2-receptor antagonists but they are not yet practically used in therapy.

Ketanserin is a serotonin 2-receptor antagonist and also strong $\alpha_1$-receptor antagonist, and hypotensive activity thereof is believed to be attributed to the $\alpha_1$-receptor antagonistic activity On the other hand, strong hypotensive activity is unfavorable for some ischemic heart diseases, such as acute myocardial infarction. From this viewpoint, Ketanserin having strong $\alpha_1$-receptor antagonistic activity is not useful for the treatment of ischemic heart diseases.

From the same reason, Irindalone having strong hypotensive activity due to $\alpha_1$-receptor antagonistic activity is also unfavorable.

While Ritanserin shows weak $\alpha_1$-receptor antagonistic activity, it is known to have a neuroleptic activity and is therefore an unsuitable drug for circulatory diseases.

Thus, most conventional serotonin 2-receptor antagonists have many pharmacological activities such as $\alpha_1$-receptor antagonistic activity and neuroleptic activity other than the objective activity.

SUMMARY OF THE INVENTION

An object of this invention is to provide a compound having highly selective serotonin 2-receptor antagonistic activity over other activities, particularly $\alpha_1$-receptor antagonistic activitY, and being useful as a preventing or treating agent for heart diseases, etc.

The inventors have extensively investigated and, as a result, found that the above object of this invention is accomplished by a heterocyclic compound represented by formula (I) shown below.

This invention relates to a heterocyclic compound represented by formula (I):

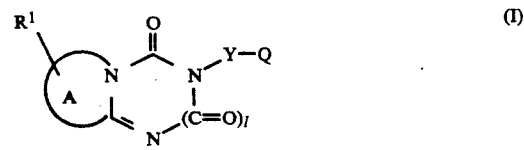

wherein $R^1$ represents a hydrogen atom, an alkyl group, an aryl group which may be substituted with one or more substituents selected from the group consisting of a halogen atom, an alkoxy group, an alkyl group and a trihalogenomethyl group; $\lambda$ represents 0 or 1; ring A represents a 5- to 7-membered heterocyclic ring which may contain one or more hetero atoms selected from the group consisting of a nitrogen atom, an oxygen atom and a sulfur atom in addition to the nitrogen atom shared with the triazine ring or triazole ring, and which may contain one or more double bonds; Y represents a substituted or unsubstituted alkylene group having from 1 to 15 carbon atoms; and Q represents a group represented by formula (II):

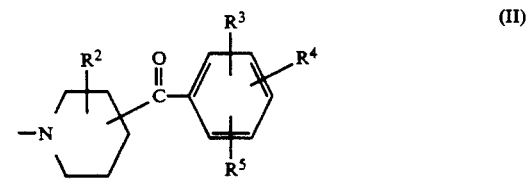

wherein $R^2$ represents a hydrogen atom, a hydroxyl group, an alkyl group or an aryl group which may be substituted with one or more substituents selected from the group consisting of a halogen atom, a hydroxyl group, an alkyl group, an alkoxy group and a trihalogenomethyl group; and $R^3$, $R^4$ and $R^5$, which may be the same or different, each represents a hydrogen atom, a halogen atom, an alkyl group, an alkoxy group, an alicyclic heterocyclic group or a trihalogenomethyl group, or a group represented by formula (III):

wherein $Ar^1$ and $Ar^2$, which may be the same or different, each
aryl group or an aromatic heterocyclic group, each of which may be substituted with one to three substituents selected from the group consisting of a halogen atom, a hydroxyl group, an alkoxy group, an alkyl group and a trihalogenomethyl group, or salts thereof.

The present invention further relates to an intermediate of the above-described heterocyclic compound of formula (I).

The present invention furthermore relates to a setonine-2 receptor antagonist or a preventing or treating agent for heart diseases, which contains the compound of formula (I) or salts thereof as an active ingredient.

The heart diseases on which the compound of the present invention is effective include angina pectoris, myocardial infarction, heart failure, restenosis after percutaneous transluminal coronary angioplasty and arrhythmia.

DETAILED DESCRIPTION OF THE INVENTION

In formula (I), the alkyl group contains from 1 to 6 carbon atoms and includes methyl, ethyl, isopropyl, n-propyl, t-butyl, n-butyl groups and the like. The halogen atom includes fluorine, chlorine, bromine and iodine atoms. The trihalogenomethyl group is a methyl grou substituted with three halogen atoms (e.g., fluorine, chlorine, bromine, and iodine) and includes trichloromethyl, trifluoromethyl groups and the like. The alkoxy group contains from 1 to 6 carbon atoms and includes methoxy, ethoxy, propoxy, butoxy groups and the like.

Ring A fuses with the triazine or triazole ring with sharing a nitrogen atom and a carbon atom together, and includes 5- to 7-membered aromatic or aliphatic heterocyclic rings, which contain one or more, preferably to three hetero atoms and may contain one or more, preferably two double bond, e.g., pyridine, 1,2-dihydropyridine, 1,2,3,4-tetrahydropyridine, 1,2,3,6-tetrahydropyridine, pyrazine, 1,2-dihydropyrazine, 1,2,3,4-tetrahydropyrazine, 1,2,3,6-tetrahydropyrazine, pyrrole, pyrroline, piperidine, homopiperidine, pyrrolidine, piperazine, homopiperazine, azepine, 1,2-dihydroazepine, 1,2,3,4-tetrahydroazepine, 1,2,3,6-tetrahydroazepine, pyrimidine, 1,2-dihydropyrimidine, 3,4-dihydropyrimidine, 1,2,3,4-tetrahydropyrimidine, 2,3,4,5-tetrahydropyrimidine, 3,4,5,6-tetrah-ydropyrimidine, imidazole, imidazoline, imidazolidine, thiazole, thiazoline, thiazolidine, pyrazole, pyrazoline, pyrazolidine, oxazole, oxazoline, oxazolidine, isothiazole, isothiazoline, isothiazolidine, isoxazole, isoxazoline, isoxazolidine, triazole, triazoline, triazolidine, 1,4-oxazine, 2,3-dihydro-1,4-oxazine, morpholine, 1,3-oxazine, 2,3-dihydro-1,3-oxazine, 2,3,4,5-tetrahydro-1,3-oxazine, 1,4-thiazine, 1,3-thiazine, 3,4-dihydro-1,2,3-triazine, 1,3,5-triazine, 1,2-dihydro-1,3,5-triazine, 1,2,4-triazine, 2,3-dihydro-1,2,4-triazine and the like.

The aryl group includes phenyl, naphthyl and biphenyl groups and the like, and usually the aryl group may be substituted with one or more, preferably to three substituents.

The aromatic heterocyclic group in formula (III) includes pyridyl, pyrimidinyl, thienyl, furyl, pyrazolyl, imidazolyl, thiazolyl, oxazolyl, isothiazolyl, isoxazolyl groups and the like.

The alkylene group includes a methylene or polymethylene group which may be substituted with one or more alkyl groups. Specific examples of the alkylene group include methylene, ethylene, propylene, butylene, pentylene, ethylethylene, trimethylene, tetramethylene, hexylene, and heptylene groups, and a group of the following formula:

wherein $R^6$ represents a hydrogen atom, an alkyl group, an aryl group which may be substituted with one or more substituents selected from the group consisting of a halogen atom, an alkoxy group, an alkyl group and a trihalogenomethyl group; and n and m each represents 0 or an integer of from 1 to 6.

The alicyclic heterocyclic group for $R_3$, $R_4$ and $R_5$ includes 5- to 7-membered heterocyclic group derived from the alicyclic heterocyclic ring referred for ring A.

Salts of the compound of formula (I), particularly, pharmaceutically acceptable salts thereo include acid addition salts formed with inorganic acids, e.g., hydrochloric acid, sulfuric acid, nitric acid, and phosphoric acid, organic acids, e.g., methanesulfonic acid, benzenesulfonic acid, toluenesulfonic acid, tartaric acid, maleic acid, fumaric acid, malic acid, oxalic acid, lactic acid, citric acid and the like.

The compound of formula (I) preferably includes those represented by formulae (IV), (V) and (VI):

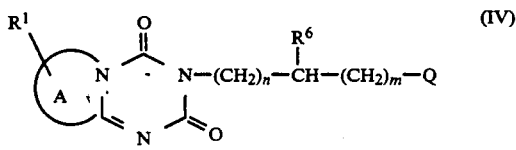

wherein ring A, $R^1$, $R^6$, Q, m, and n are as defined above.

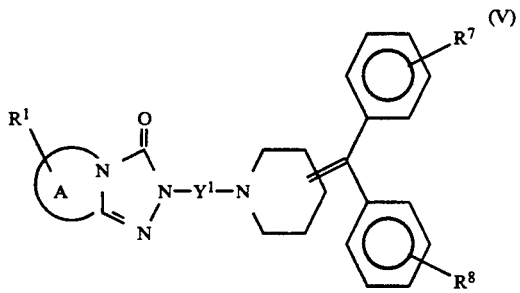

wherein ring A and $R^1$ are as defined above; $R^7$ and $R^8$, which may be the same or different, each represents a hydrogen atom, a hydroxyl group, an alkyl group, an alkoxy group, a halogen atom or a trihalogenomethyl group; $Y^1$ represents an alkylene group having from 2 to 7 carbon atoms.

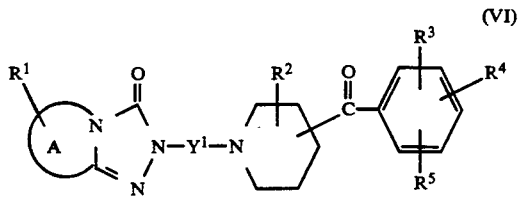

wherein ring A, $R^1$, $R^2$, $R^3$, $R^4$, $R^5$ and $Y^1$ are as defined above.

Of the compounds represented by formula (I), particularly preferred are those wherein ring A is a pyrrolidine or a piperidine, a homopiperidine or a thiazole; Y is an alkylene group having 1 to 6 carbon atoms; and Q is a group represented by formula (II') or (III'):

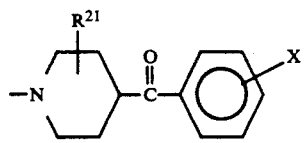

wherein $R^{21}$ represents a hydrogen atom or a hydroxyl group; and X represents a halogen atom.

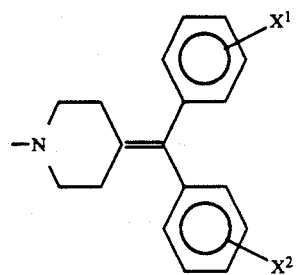

wherein $X^1$ and $X^2$, which may be the same or different, each represents a halogen atom.

In the above (V) and (VI), the alkylene group as represented by $Y^1$ is a methylene or polymethylene group which may be substituted with one or more alkyl groups, and examples thereof includes methylene, ethylene, propylene, butylene, pentylene, hexylene, ethylethylene, trimethylene, tetramethylene groups and the like.

Of the compound of formula (I), most preferred is 3-[2-[4-(4-fluorobenzoyl)piperidin-1-yl]ethyl]-6,7,8,9,-tetrahydro-2H-pyrido[1,2-a]-1,3,5-triazine-2,4(3H)-dione or acid addition salts thereof.

The heterocyclic compound represented by formula (I) can be prepared by many processes. Typical processes thereof are as follows.

1) Process A

The heterocyclic compound of formula (I) can be prepared by reacting a compound represented by formula (VII):

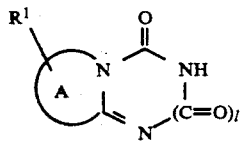

wherein $R^1$, ring A and λ are as defined above, with a compound of formula (VIII):

HO—Y—Q    (VIII)

wherein Q and Y are as defined above, in a solvent, e.g., dimethylformamide, tetrahydrofuran and dioxane, in the presence of dehydrating reagents, for example, a mixture of triphenylphosphine and a dialkyl azodicarboxylate, at a temperature of from 0° C. to the boiling point of the solvent for several minutes to several days. The compound of formula (VIII) and dehydrating reagents can be used in equimolar excess amount to the compound of formula (VII).

The compound of formula (I) can also be prepared by reacting the compound of formula (VII) or salts thereof with a compound represented by formula (IX):

$X^3$—Y—Q    (IX)

wherein Y and Q are as defined above; and $X^3$ represents a halogen atom, a trifluoromethanesulfonyloxy group, an alkylsulfonyloxy group or an arylsulfonyloxy group which may be substituted with an alkyl group, a halogen atom or an alkoxy group in the aryl group moiety thereof, in the presence of a base, e.g., an alkali metal carbonate (e.g., potassium carbonate and sodium carbonate), an alkali metal hydride (e.g., sodium hydride and potassium hydride), and an organic base (e.g., triethylamine and 1,8-diazacyclo[5.4.0]-7-undecene), in an organic solvent, e.g., ethanol, methanol, dimethylformamide, tetrahydrofuran, dioxane, and benzene, at a temperature of from room temperature to the boiling point of the solvent for 0.5 hours to several days. The reaction may be carried out in the presence of from a catalytic amount to equimolar excess amount of an alkali metal iodide, e.g., sodium iodide and potassium iodide to the compound of formula (VII). The compound of formula (IX) and base can be used in equimolar excess amount to the compound of formula (VII). The above arylsulfonyloxy group include p-toluenesulfonyloxy group and pbromophenylsulfonyloxy group, preferably p-toluenesulfonyloxy group.

Some of the intermediate compounds represented by formula (VII), wherein λ is 1, are known. For example, 2-Hpyrido[1,2-a]-1,3,5-triazine-2,4(3H)-dione, 6-methyl-2H-oxazolo [3,2-a]1,3,5-triazine-2,4(3H)-dione, and 8-methylimidazo[1,2,-a]-1,3,5-triazine-2,4(3H,8H)-dione are disclosed in West German OLS 1922837, *Synthesis*, p. 892 (1985), British Patent 1328205, and *Journal of Organic Chemistry*, Vol. 43, p. 4774 (1978), respectively. The compounds of formula (VII) can be prepared by referring to the processes disclosed in the above-described literatures.

In general, the compound of formula (VII) wherein λ is 1 can be prepared by reacting a compound represented by formula (X):

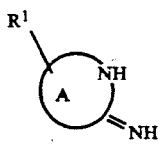

wherein $R^1$ and ring A are as defined above, with phenoxycarbonylisocyanate or diphenyl imidocarboxylate in a solvent, e.g., dimethylformamide, tetrahydrofuran, acetonitrile and dioxane, at a temperature of from 0° C. to the boiling point of the solvent.

Also, most of compound of formula (VII) wherein λ is 0 are known and can be prepared according to processes described in *Boll. Chim. Farm.*, Vol. 113, p. 152 (1974), *Chem. Ber.*, Vol. 90, p. 909 (1957) and *Chem. Ber.*, Vol. 103, p. 1934 (1970).

2) Process B

The compound of formula (I) can be prepared by reacting a compound represented by formula (XI):

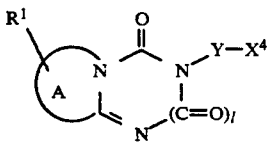

wherein $R^1$, ring A, λ and Y are as defined above; and $X^4$ represents a halogen atom, a trifluoromethanesulfonyloxy group, an alkylsulfonyloxy group or an arylsulfonyloxy group which may be substituted with an alkyl group, an alkoxy group or a halogen atom in the aryl group moiety thereof with a compound represented by formula (XII or salts thereof:

H—Q  (XII)

wherein Q is as defined above, in a solvent, e.g., benzene, toluene, acetonitrile, chloroform, dichloroethane, dimethylformamide, tetrahydrofuran and dioxane, in the presence of a base, e.g., triethylamine, dimethylaniline, 1,8-diazabicyclo[5.4.0]-7-undecene, potassium carbonate, sodium carbonate, sodium hydride, and potassium hydride, at a temperature of from room temperature to the boiling point of the solvent for 0.5 hours to several days. If desired, this reaction may be carried out in the presence a catalytic amount to equimolar excess amount of an alkali metal iodide, e.g., sodium iodide and potassium iodide to the compound of formula (XI). The compound of formula (XII) and base can be used in equimolar excess amount to the compound of formula (XI).

Of the starting compound of formula (XI), the compound wherein λ is 0 is a novel compound and can be prepared by processes described in Reference Examples hereinafter given or an appropriate combination of known processes, such as those described in *Boll. Chim. Farm.*, Vol. 113, p. 152 (1974), *Chem. Ber.*, Vol. 90, p. 909 (1957), and *Chem. Ber.*, Vol. 103, p. 1934 (1970).

Also, of the compound of formula (XI), the compound wherein λ is 1 can be prepared by processes in Reference Examples or processes as follows.

consisting of a halogen atom, an alkyl group, an alkoxy group and a nitro group.

That is, the compound of formula (VIIa) can be reacted with a compound of HO—Y—$X^4$ in the presence of triphenylphosphine and diethylazodicarboxylate in an organic solvent at a temperature of −30° C. to a boiling point of a used solvent to give the objective compound of formula (XIa). Also, the compound of formula (X) can be reacted with the compound of formula (XIII) in organic solvent at a temperature of a room temperature to a boiling point of a used solvent to give a compound of formula (XIV), and the compound can be reacted with alkylsulfonylchloride, arylsulfonylchloride which may be substituted with an alkyl group, an alkoxy group or a halogen atom or halogenating agents such as thionylchloride, phosphorous chloride in the presence of an organic base such as triethylamine, dimethylaniline, 1,8-diazabicyclo[5.4.0]-7-undecene in an organic solvent to give the objective compound of formula (XIa).

When the compound of formula (I) according to the present invention was orally administered to rats for consecutive 10 days, no case of death was observed at a dose level of 800 mg/kg, proving that the compound of formula (I) and salts thereof are of high safety.

The compound of formula (I) or a salt thereof can be formulated into various dose forms, such as tablets, powders, capsules, and injectable solutions by conventional techniques using appropriate additives such as lactose, corn starch, crystalline cellulose, polyvinyl alcohol, carboxymethyl cellulose calcium, magnesium stearate, talc and the like. The compound of formula (I) and salts thereof can be generally administered orally, subcutaneously, intramuscularly or intravenously.

The compound of formula (I) or a salt thereof is usually administered at a dose of from 30 to 2,000 mg/day for adult when orally given.

The compound according to the present invention and salts thereof exhibit potent and long-lasting serotonin 2-receptor antagonistic activity, while having weak $α_1$-receptor antagonistic activity. Therefore, they have excellent selectivity in their serotonin 2-receptor antagonistic activity the selectivity being higher than that of

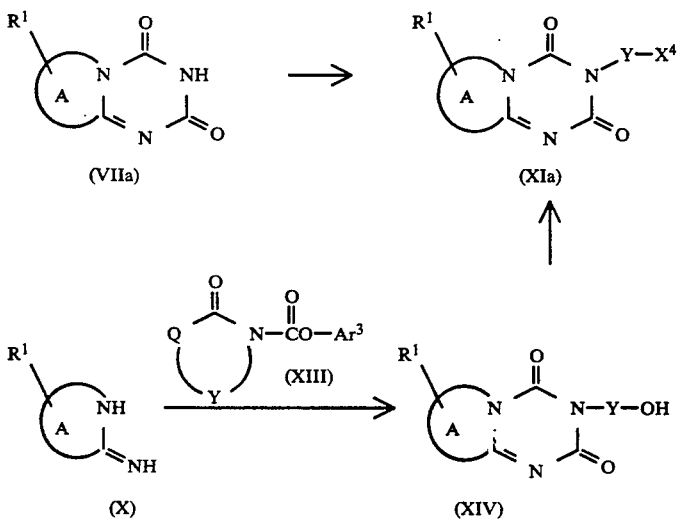

wherein ring A, $R^1$, Y and $X^4$ are as defined above, and $Ar^3$ represents an aryl group which may be substituted with one or more substituents selected from the group Ketanserin, and the activity being higher than that of Ritanserin. Further, the compound of the invention and salts thereof have lower toxicity than Ketanserin and weak neuroleptic activity. Accordingly, the compound of formula (I) and salts thereof are very excellent as a serotonin 2-receptor antagonist or a drug for circulatory diseases.

In particular, the compound of formula (I) and salts thereof experimentally exhibited excellent activities in improvement of cardiac functions, improvement on myocardium necrosis, prevention of coronary thrombus formation, improvement of cardiac microcirculation, and the like in heart disease animal models, such as an angina pectoris model, a myocardial infarction model, etc. Thus, the compound of formula (I) and salts thereof ar excellent as a preventing and treating agent for heart diseases, particularly ischemic heart diseases.

The present invention is now illustrated in greater detail by way of Reference Examples, Examples, and Test Examples, but it should be understood that the present invention is not deemed to be limited thereto.

EXAMPLE 1

Synthesis of 3-[2-[4-(4-Fluorobenzoyl)piperidin-1-yl]ethyl]-6,7,8,9-tetrahydro-2H-pyrido1,2-a1-1,3,5-triazine-2,4(3H)-dione 1) 6,7,8,9-Tetrahydro-2H-pyrido[1,2-a1-1,3,5-triazine-2,4(3H)-dione To an ethanol solution of sodium ethoxide prepared from 0.83 g of metallic sodium and 40 mλ of absolute ethanol was added 4.8 g of 2-amino-3,4,5,6-tetrahydropyridine hydrochloride under ice-cooling, followed by stirring at room temperature for 30 minutes. The insoluble material wa removed s by filtration, and the filtrate was concentrated to dryness under reduced pressure. The residue was suspended in 30 mλ of tetrahydrofuran, and 5.9 g of phenoxycarbonylisocyanate was added dropwise to the suspension with stirring under icecooling over 10 minutes. After allowing to stand at room temperature overnight, the precipitated material was filtered to give 1.4 g of the entitled compound. The filtrate was concentrated to dryness under reduced pressure, and the residue was applied to a column contained with 100 g of silica gel, then eluted with chloroform containing 5% methanol t obtain 2.04 g of the entitled compound. The two crops were combined to yield 3.44 g of the entitled compound as colorless crystals.

Melting Point: 185°–187° C.

NMR Spectrum (DMSO-d$_6$) δ: 1.6–1.9 (4H, m), 2.65 (2H, t), 3.64 (2H, t), 11.39 (1H, b)

IR Spectrum ν (KBr) cm$^{-1}$: 3450, 3200, 3070, 1700, 1590, 1490, 1440, 1390

Elemental Analysis for C$_7$H$_9$N$_3$O$_2$: Calcd. (%): C 50.30; H 5.43; N 25.14. Found (%): C 50.37; H 5.45; N 24.91.

2) 3-[2-[4-(4-Fluorobenzoyl)piperidin-1-yl]ethyl]-6,7,8,9-tetrahydro-2H-pyrido[1,2-a]-1,3,5-triazine-2,4(3H)-dione In 900 mλ of tetrahydrofuran were suspended 34.1 g of 6,7,8,9-tetrahydro-2H-pyrido[1,2-a]-1,3,5-triazine-2,4(3H)-dione prepared in 1) above, 51.2 g of 4-(4-fluorobenzoyl)-1(2-hydroxyethyl)piperidine and 56.1 g of triphenylphosphine, and 38 g of diethyl azodicarboxylate was added dropwise thereto under ice-cooling over 15 minutes. After stirring at room temperature for 20 minutes, the reaction mixture was concentrated to dryness under reduced pressure, and to the residue was added 500 mλ of ethyl acetate. The reaction mixture was extracted with 1N hydrochloric acid, and the extract was made alkaline with potassium carbonate and then extracted with chloroform. The chloroform solution was dried over anhydrous sodium sulfate, and then concentrated to dryness under reduced pressure. The residue was crystallized from ethanol and then recrystallized from a mixed solvent of methanol and ethanol to obtain 33.7 g of the entitled compound as colorless crystals.

Melting Point: 170°–172° C.

NMR Spectrum (CDCλ$_3$) δ: 1.8–2.2 (10H, m), 2.26 (2H, t), 2.81 (2H, t), 3.0–3.3 (3H, m), 3.84 (2H, t), 4.06 (2H, t), 7.13 (2H, t), 7.95 (2H, dd)

IR Spectrum ν (KBr) cm$^{-1}$: 1730, 1670, 1600, 1490, 1450, 1410

Elemental Analysis for C$_{21}$H$_{25}$FN$_4$O$_3$: Calcd. (%): C 62.99; H 6.29; N 13.99. Found (%): C 62.68; H 6.28; N 13.83.

EXAMPLE 2

Synthesis of 3-[2-[4-(4-Fluorobenzoyl)piperidin-1-yl]ethyl]-6,7,8,9-tetrahydro-2H-pyrido[1,2-a]-1,3,5-triazine-2,4(3H)-dione Hydrochloride In 150 mλ of hot ethanol was dissolved 33.0 g of 3-[2-[4-(4-fluorobenzoyl)piperidin-1-yl]ethyl]-6,7,8,9-tetrahydro-2H-pyrido[1,2-a]-1,3,5-triazine-2,4(3H)-dione as prepared in Example 1, and 15 mλ of concentrated hydrochloric acid was added to the solution. After cooling, the precipitated crystals were collected by filtration and recrystallized from ethanol to obtain 27.4 g of the entitled compound as colorless crystals.

Melting Point: 256°–259° C. (decomposition)

NMR Spectrum (D$_2$O) δ: 1.4–2.4 (8H, m), 2.86 (2H, t), 3.1–4.0 (9H, m), 4.37 (2, t), 7.30 (2H, t), 8.07 (2H, dd)

IR Spectrum ν (KBr) cm$^{-1}$: 3450, 2940, 2510, 1730, 1670, 1600, 1480, 1420

Elemental Analysis for C$_{21}$H$_{25}$FN$_4$O$_3$·HCλ: Calcd. (%): C 57.73; H 6.00; N 12.82. Found (%): C 57.50; H 5.82; N 12.59.

EXAMPLE 3

Synthesis of 3-[2-[4-(4-Fluorobenzoyl)piperidin-1-yl]ethyl]-6,7,8,9-tetrahydro-2H-pyrido1,2-a]-1,3,5-triazine-2,4(3H)-dione Maleate In 50 mλ of methanol was dissolved 2.0 g of 3-[2-[4-(4-fluorobenzoyl)piperidin-1-yl]ethyl]-6,7,8,9-tetrahydro-2H-pyrido[1,2-a]-1,3,5-triazine-2,4(3H)-dione prepared in Example 1, and 0.58 g of maleic acid was added to the solution. The solution was concentrated under reduced pressure, and the precipitated crystals were collected by filtration, followed by recrystallization from 90% aqueous ethanol to give 1.27 g of the entitled compound as colorless crystals.

Melting Point: 180°–183° C. (decomposition)

NMR Spectrum (DMSO-d$_6$) δ: 1.6–2.1 (8H, m), 2.71 (2H, t), 2.9–3.4 (4H, m), 3.5–3.8 (5H, m), 4.12 (2H, m), 6.06 (2H, s), 7.39 (2H, t), 8.10 (2H, dd)

IR Spectrum ν KBr) cm$^{-1}$: 3448, 1734, 1677, 1596, 1494, 1455

Elemental Analysis for C$_{21}$H$_{25}$FN$_4$O$_3$·C$_4$H$_4$O$_4$: Calcd. (%): C 58.13; H 5.66; N 10.85.Found (%): C 58.28; H 5 64; N 10.87.

EXAMPLE 4

Synthesis of 3-[2-[4-(4-Fluorobenzoyl)piperidin-1-yl]ethyl]-7,8-dihydro-2H,6H-pyrrolo[1,2-a]-1,3,5-triazine-2,4(3H)-dione 1) 7,8-Dihydro-2H,6H-pyrrolo[1,2-a]-1,3,5-triazine-2,4(3H)-dione In the manner described in Example 1—1), the entitled compound was obtained as colorless crystals from 2-iminopyrrolidine hydrochloride and phenoxycarbonylisocyanate.

Melting Point: 201°–202° C.

NMR Spectrum (DMSO-$d_6$): 2.87 (2H, t), 2.07 (2H, t), 3.82 (2H, t), 11.25 (1H, bs)

IR Spectrum $\nu$ (KBr) cm$^{-1}$: 3430, 3210, 3080, 1740, 1710, 1690, 1630, 1440, 1410

Elemental Analysis for $C_6H_7N_3O_2$: Calcd. (%): C 47.06; H 4.61; N 27.44. Found (%): C 47.15; H 4.40; N 27.33.

2) 3-[2-4-(4-Fluorobenzoyl)piperidin-1-yl]ethyl]-7,8-dihydro-2H,6H-pyrrolo[1,2-a]-1,3,5-triazine-2,4(3H)-dione In the manner described in Example 1-2), 7,8-dihydro-2H,6H-pyrrolo[1,2-a]-1,3,5-triazine-2,4(3H)-dione prepared in 1) above and 4-(4-fluorobenzoyl)-1-(2-hydroxyethyl)piperidine were condensed in N,N-dimethylformamide in the presence of triphenylphosphine and diethyl azodicarboxylate to obtain the entitled compound as a caramel-like substance.

NMR Spectrum (CDCl$_3$) δ: 1.7–1.9 (4H, m), 2.1–2.5 (4H, m), 2.68 (2H, t), 2.9–3.4 (5H, m), 4.05 (4H, t-like), 7.12 (2H, t), 7.95 (2H, dd)

EXAMPLE 5

Synthesis of 3-[2-[4-(4-Fluorobenzoyl)piperidin-1-yl]ethyl]-7,8-dihydro-2H,6H-pyrrolo[1,2-a]-1,3,5-triazine-2,4(3H)-dione Hydrochloride Hemihydrate In 50 mλ of methanol was dissolved 2.95 g of 3-[2-[4-(4-fluorobenzoyl)piperidin-1-yl]ethyl]-7,8-dihydro-2H,6H-pyrrolo[1,2-a]-1,3,5-triazine-2,4(3H)-dione prepared in Example 4-2), and 2 mλ of concentrated hydrochloric acid was added thereto, followed by concentration to dryness under reduced pressure. The residue was crystallized from ethanol to obtain 2.30 g of the entitled compound as a colorless powder.

Melting Point: 253°–255° C.

NMR Spectrum (DMSO-$d_6$) δ: 1.8–2.3 (6H, m), 2.91 (2H, t), 3.0–3.5 (4H, m) 3.5–4.0 (5H, m), 4.16 (2H, t), 7.37 (2H, t), 8.09 (2H, dd), 10.68 (1H, b)

IR Spectrum $\nu$ (KBr) cm$^{-1}$: 3560, 2940, 2510, 1730, 1680, 1630, 1480, 1450, 1420

Elemental Analysis for $C_{20}H_{23}FN_4O_3 \cdot HCl \cdot \frac{1}{2}H_2O$: Calcd. (%): C 55.62; H 5.83; N 12.97. Found (%): C 55.69; H 5.80; N 12.83.

EXAMPLE 6

Synthesis of 3-[2-[4-(4-Fluorobenzoyl)piperidin-1-yl]ethyl]-7,8,9,10-tetrahydro-2H,6H-1,3,5-triazino[1,2-a]azepine-2,4(3H)-dione 1) 7,8,9,10-Tetrahydro-2H,6H-1,3,5-triazino[1,2-a]azeoine-2,4(3H)-dione Monohydrate In the manner described in Example 1—1), the entitled compound was prepared as a colorless powder from 3,4,5,6-tetrahydro-7-amino-2H-azepine hydrochloride and phenoxycarbonylisocyanate.

Melting Point: 157°–158° C.

NMR Spectrum (CDCl$_3$) δ: 1.7 6H, m), 2.8 (2H, m), 4.0 (2H, m), 11.0 (1H, bs)

IR Spectrum $\nu$ (KBr) cm$^{-1}$: 3520, 3200–2800, 1730, 1670, 1600, 1480, 1420

Elemental Analysis for $C_8H_{11}FN_3O_2 \cdot H_2O$: Calcd. (%): C 48.24; H 6.58; N 21.09. Found (%): C 48.33; H 6.42; N 21.02.

2) 3-[2-[4-(4-Fluorobenzoyl piperidin-1-yl]ethyl]-7,8,9,10-tetrahydro-2H,6H-1,3,5-triazino[1,2-a]azepine-2,4(3H)-dione In the manner described in Example 1-2), 7,8,9,10-tetrahydro-2H,6H-1,3,5-triazino[1,2-a]azepine-2,4(3H)-dione prepared in 1) above was condensed with 4-(4-fluorobenzoyl)-1-(2-hydroxyethyl)piperidine in N,N-dimethylformamide in the presence of triphenylphosphine and diethyl azodicarboxylate to obtain the entitled compound as colorless crystals.

Melting Point: 130°–132° C.

NMR Spectrum (CDCl$_3$) δ: 1.6–2.0 (10H, m), 2.0–2.4 (2H, m), 2.69 (2H, t), 3.0–3.3 (3H, m), 4.0–4.2 (4H, m), 7.13 (2H, t), 7.95 (2H, dd)

IR Spectrum $\nu$ (KBr) cm$^{-1}$: 3440, 2950, 1725, 1670, 1600, 1470,

EXAMPLE 7

Synthesis of 3-[2-[4-(4-Fluorobenzoyl)piperidin-1-yl]ethyl]-7,8,9,10-tetrahydro-2H,6H-1,3,5-triazino[1,2-a]azepine-2,4(3H)-dione Dihydrochloride In 50 mλ of methanol was dissolved 3.63 g of 3-[2-[4-(4-fluorobenzoyl)piperidin-1-yl]ethyl]-7,8,9,10-tetrahydro-2H,6H-1,3,5-triazino[1,2-a]azepine-2,4(3H)-dione prepared in Example 6, and 1.6 mλ of concentrated hydrochloric acid was added thereto, followed by concentration to dryness under reduced pressure. Ethanol was added to the residue, the mixture was concentrated under reduced pressure several times, and the residue was crystallized from a mixture of ethanol and isopropyl ether to obtain 3.70 g of the entitled compound as a colorless powder.

Melting Point: 172°–176° C.

NMR Spectrum (DMSO-$d_6$) δ: 1.6–2.2 (10H, m), 2.8 (2H, m), 3.0–3.5 (4H, m), 3.5–3.9 (3H, m), 4.0–4.2 (4H, m), 7.37 (2H, t), 8.12 (2H, dd), 11.0 (1H, b)

IR Spectrum $\nu$ (KBr) cm$^{-1}$: 3450, 2940, 2360, 1770, 1725, 1680, 1610, 1580, 1450, 1430, 1230

Elemental Analysis for $C_{22}H_{27}FN_4O_3 \cdot 2HCl$: Calcd. (%): C 54.21; H 6.00; N 11.50. Found (%): C 54.12; H 6.33; N 11.42.

EXAMPLE 8

Synthesis of
3-[3-[4-(4-Fluorobenzoyl)piperidin-1-yl)propyl]-6,7,8,9-tetrahydro-2H-pyrido[1,2-a]-1,3,5-triazine-2,4(3H)-dione In the manner described in Example 1-2), 6,7,8,9-tetrahydro-2H-pyrido[1,2-a]-1,3,5-triazine-2,4(3H)-dione prepared in Example 1-1) and 4-(4-fluorobenzoyl)-1-(3-hydroxypropyl)piperidine were condensed in N,N-dimethylformamide in the presence of triphenylphosphine and diethyl azodicarboxylate to obtain the entitled compound as an oily substance.

NMR Spectrum (CDC$\lambda_3$) $\delta$: 1.5$\propto$2.1 (12H, m), 2.50 (2H, t), 2.7–3.1 (4H, m), 3.2 (1H, m), 3.85 (2H, t), 4.02 (2H, t), 7.13 (2H, t), 7.95 (2H, dd)

EXAMPLE 9

Synthesis of
3-[3-[4-(4-Fluorobenzoyl)piperidin-1-yl]propyl]-6,7,8,9-tetrahydro-2H-pyrido[1,2-a]-1,3,5-triazine-2,4(3H)-dione Maleate Hemihydrate In 100 m$\lambda$ of hot ethanol was added 0.76 g of 3-[3-[4-(4-fluorobenzoyl)piperidin-1-yl]propyl]-6,7,8,9-tetrahydro-2H-pyrido[1,2-a]-1,3,5-triazine-2,4(3H)-dione prepared in Example 8, and 0.21 g of maleic acid was added thereto. The precipitated crystals were collected by filtration and recrystallized from ethanol to obtain 0.42 g of the entitled compound as colorless crystals.

Melting Point: 87°–89° C.

NMR Spectrum (DMSO-d$_6$) $\delta$: 1.6–2.2 (10H, m), 2.70 (2H, t), 2.9–3.3 (4H, m), 3.4–4.0 (7H, m), 6.04 (2H, s), 7.39 (2H, t), 8.10 (2H, dd)

IR Spectrum $\nu$ (KBr) cm$^{-1}$: 3450, 2970, 1730, 1680, 1600, 1490

Elemental Analysis for C$_{22}$H$_{27}$FN$_4$O$_3$·C$_4$H$_4$O$_4$·½H$_2$O: Calcd. (%): C 57.88; H 5.98; N 10.38. Found (%): C 57.50; H 6.30; N 10.18.

EXAMPLE 10

Synthesis of
3-[2-[4-(4-Fluorobenzoyl)-4-hydroxypiperidin-1-yl]ethyl]-6,7,8,9-tetrahydro-2H-pyrido[1,2-a]-1,3,5-triazine-2,4(3H)-dione In the manner described in Example 1-2), 6,7,8,9-tetrahydro-2H-pyrido[1,2-a]-1,3,5-triazine-2,4(3H)-dione obtained in Example 1-1) and 4-(4-fluorobenzoyl)-4-hydroxy-1-(2-hydroxyethyl)piperidine were condensed in N,N-dimethylformamide in the presence of triphenylphosphine and diethyl azodicarboxylate to obtain the entitled compound as colorless crystals.

Melting Point: 217°–220° C.

NMR Spectrum (CDC$\lambda_3$) $\delta$: 1.6–2.0 (8H, m), 2.3–2.7 (8H, m), 3.68 (2H, t), 3.87 (2H, t), 5.68 (1H, s), 7.28 (2H, t), 8.24 (2H, dd)

IR Spectrum $\nu$ (KBr) cm$^{-1}$: 3450, 2960, 1730, 1670, 1600, 1490, 1450, 1410

EXAMPLE 11

Synthesis of
3-[2-[4-(4-Fluorobenzoyl)-4-hydroxy-piperidin-1-yl]ethyl]-6,7,8,9-tetrahydro-2H-pyrido[1,2-a]-1,3,5-triazine-2,4(3H)-dione Dihydrochloride Hemihydrate In 30 m$\lambda$ of methanol was dissolved 0.80 g of 3-[2-[4-(4-fluorobenzoyl)-4-hydroxypiperidin-1-yl]ethyl]-6,7,8,9-tetrahydro-2H-pyrido[1,2-a]-1,3,5-triazine-2,4(3H)-dione obtained in Example 10, and 0.4 m$\lambda$ of concentrated hydrochloric acid was added thereto, followed by concentration to dryness under reduced pressure. Ethanol was added to the residue, followed by concentration under reduced pressure repeatedly. The precipitated crystals were collected by filtration and washed with acetone to obtain 0.68 g of the entitled compound as colorless crystals.

Melting Point: 178°–184° C.

NMR Spectrum (DMSO-d$_6$) $\delta$: 1.6–2.4 (8H, m), 2.7 (2H, t), 3.0–3.6 (6H, m), 3.73 (2H, t), 4.1 (2H, t), 7.2–7.5 (3H, m), 8.77 (2H, dd), 11.0 (1H, b)

IR Spectrum $\nu$ (KBr) cm$^{-1}$: 3410, 3220, 2550, 1780, 1730, 1680, 1610, 1580, 1440

Elemental Analysis for C$_{21}$H$_{25}$FN$_4$O$_4$·2HC$\lambda$·½H$_2$O: Calcd. (%): C 50.60; H 5.66; N 11.24. Found (%): C 50.88; H 5.81; N 10.87.

EXAMPLE 12

Synthesis of
3-[2-[4-(4-Fluorobenzoyl)-4-phenylpiperidin-1-yl]ethyl]-6,7,8,9-tetrahydro-2H-pyrido[1,2-a]-1,3,5-triazine-2,4(3H)-dione In the manner described in Example 1-2), 6,7,8,9-tetrahydro-2H-pyrido[1,2-a]-1,3,5-triazine-2,4(3H)-dione obtained in Example 1-1) and 4-(4-fluorobenzoyl)-4-phenyl-1-(2-hydroxyethyl)piperidine were condensed in N,N-dimethylformamide in the presence of triphenylphosphine and diethyl azodicarboxylate to obtain the entitled compound as an oily substance.

NMR Spectrum (CDC$\lambda_3$) $\delta$: 1.8–2.9 (16H, m), 3 8 (2H, t-like), 4.03 (2H, t), 6.89 (2H, t), 7.26–7.48 (7H, m)

EXAMPLE 13

Synthesis of
3-[2-[4-(4-Fluorobenzoyl)-4-phenylpiperidin-1-yl]ethyl]-6,7,8,9-tetrahydro-2H-pyrido[1,2-a]-1,3,5-triazine-2,4(3H)-dione Dihydrochloride Hemihydrate In 30 m$\lambda$ of methanol was dissolved 0.75 g of 3-[2-[4-(4-fluorobenzoyl)-4-phenylpiperidin-1-yl]ethyl]-6,7,8,9-tetrahydro-2H-pyrido[1,2-a]-1,3,5-triazine-2,4(3H)-dione obtained in Example 12, and 0.3 m$\lambda$ of concentrated hydrochloric acid was added thereto, followed by concentration to dryness under reduced pressure. To the residue was added ethanol, followed by concentration to dryness under reduced pressure repeatedly. The residue was recrystallized from a mixture of methanol and ethanol to obtain 0.52 g of the entitled compound as a colorless powder.

Melting Point: 203°–210° C.

NMR Spectrum (DMSO-d$_6$) $\delta$: 1.6–2.0 (4H, m), 2.4–3.1 (8H, m), 3.3 (2H, m), 3.5–3.7 (4H, m), 4.1 (2H, t), 7.1–7.7 (9H, m), 11.2 (1H, b)

IR Spectrum $\nu$ (KBr) cm$^{-1}$: 3410, 2960, 2490, 1770, 1730, 1680, 1620, 1580, 1500, 1440

Elemental Analysis for C$_{27}$H$_{29}$FN$_4$O$_3$·2HC$\lambda$·½H$_2$O: Calcd. (%): C 58.07; H 5.77; N 10.03. Found (%): C 58.28; H 6.04; N 9.70.

EXAMPLE 14

Synthesis of
3-[2-[4-(4-Fluorobenzoyl)-piperidin-1-yl]ethyl]-2H-pyrido[1,2-a]-1,3,5-triazine-2,4(3H)-dione Dihydrochloride In 10 m$\lambda$ of N,N-dimethylformamide were suspended 0.42 g of 2H-pyrido[1,2-a]-1,3,5-triazine-2,4(3H)-dione, 0.67 g of 4-(4-fluorobenzoyl)-1-(2-hydroxyethyl)- piperidine and 0.82 g of triphenylphosphine, and 0.54 g of diethyl azodicarboxylate was added dropwise thereto, followed by stirring at room temperature for 75 minutes. The reaction mixture was concentrated to dryness under reduced pressure, and the residue wa crystallized from ethanol and filtered to collect 0.7 g of the base of the entitled compound. The resulting crystals were dissolved in 30 mλ of ethanol, and 0.2 mλ of hydrochloric acid was added, followed by concentration under reduced pressure. The precipitate was collected by filtration to obtain 0.27 g of the entitled compound as a colorless powder.

Melting Point: 243°–244° C. (decomposition)

NMR Spectrum (DMSO-d$_6$) δ: 1.8–2.2 (4H, m), 2.88–3.97 (7H, m), 4.38 (2H, t), 7.1–7.5 (4H, m), 8.0–8.3 (3H, m), 8.69 (1H, d), 11.02 (1H, bs)

IR Spectrum ν (KBr) cm$^{-1}$: 3430, 2700–2200, 1730, 1680, 1640, 1590, 1560, 1440, 1410

Elemental Analysis for $C_{21}H_{21}FN_4O \cdot 2HC\lambda$: Calcd. (%): C 53.74; H 4.94; N 11.94. Found (%): C 53.39; H 4.83; N 11.83.

EXAMPLE 15

Synthesis of 3-[2-[4-(4-Fluorobenzoyl)-piperidin-1-yl]ethyl]-2H-thiazolo-[3,2-a]-1,3,5-triazine-2,4(3H)-dione In 40 mλ of N,N-dimethylformamide were suspended 1.69 g of 2H-thiazolo 3,2-a]-1,3,5-triazine-2,4(3H)-dione, 2.51 g of 4-(4-fluorobenzoyl)-1-(2-hydroxyethyl)piperidine and 2.89 g of triphenylphosphine, and 1.92 g of diethyl azodicarboxylate was added dropwise thereto with stirring under ice-cooling. After stirring at room temperature for 30 minutes, the reaction mixture was concentrated to dryness under reduced pressure. Ethyl acetate was added to the residue, followed by filtration to obtain 3.0 g of the entitled compound as colorless crystals.

Melting Point: 184°–187° C.

NMR Spectrum (CDCλ$_3$) δ: 1.5–1.9 (4H, m), 2.2 (2H, m), 2.5 (2H, m), 3.0 (2H, m), 3.4 (1H, m), 3.95 (2H, t), 7.18 (1H, d), 7.34 (2H, t), 7.71 (1H, d), 8.05 (2H, dd)

IR Spectrum ν (KBr) cm$^{-1}$: 3450, 3070, 2940, 2820, 1750, 1670, 1590, 1550

EXAMPLE 16

Synthesis of 3-[2-[4-(4-Fluorobenzoyl)piperidin-1-yl]ethyl]-2H-thiazolo[3,2-a]-1,3,5-triazine-2,4(3H)-dione Hydrochloride Hemihydrate In 50 mλ of methanol was suspended 2.95 g of 3-[2-[4-(4-fluorobenzoyl)piperidin-1-yl]ethyl]-2H-thiazolo[3,2-a]-1,3,5-triazine-2,4(3H)-dione obtained in Example 15, and 2 mλ of concentrated hydrochloric acid was added to the suspension. The crystals thus precipitated wer collected by filtration and recrystallized from hot water containing a small amount of methanol to obtain 2.08 g of the entitled compound as a colorless powder.

Melting Point: 278°–280° C. (decomposition)

NMR Spectrum (DMSO-d$_6$) δ: 1.6–2.2 (4H, m), 2.9–3.8 (7H, m), 4.24 (2H, t), 7.23 (1H, d), 7.38 (2H, t), 7.92 (1H, d), 8.11 (2H, dd)

IR Spectrum ν (KBr) cm$^{-1}$: 3470, 1740, 1670, 1600, 1580, 1550, 1420

Elemental Analysis for $C_{19}H_{19}FN_4O_3S \cdot HC\lambda \cdot \frac{1}{2}H_2O$: Calcd. (%): C 50.95; H 4.73; N 12.51. Found (%): C 51.29; H 4.88; N 12.55.

EXAMPLE 17

Synthesis of 3-[2-[4-[Bis(4-fluorophenyl)-methylene]piperidin-1-yl]ethyl]-6,7,8,9-tetrahydro-2H-pyrido1,2-a]-1,3,5-triazine-2,4(3H)-dione In 50 mλ of N,N-dimethylformamide were dissolved 1.67 g of 6,7,8,9-tetrahydro-2H-pyrido[1,2-a]-1,3,5-triazine-2,4 3H)-dione obtained in Example 1-1), 3.64 g of 4-[bis(4-fluorophenyl)methylene]-1-(2-hydroxyethyl)-piperidine and 3.15 g of triphenylphosphine, and 2.1 g of diethyl azodicarboxylate was added dropwise thereto with stirring under ice-cooling. After stirring for 30 minutes, the reaction mixture was concentrated to dryness under reduced pressure, and the residue was applied to a column contained with 180 g of silica gel and eluted with 3% methanol-containing chloroform to obtain 1.38 g of the entitled compound as a yellow oily substance.

NMR Spectrum (CDCλ$_3$) δ: 1.8–2.0 (4H, m), 2.3 (4H, m), 2.5–2.8 (8H, m), 3.8 (2H, t), 4.07 (2H, t), 6.96 (4H, d), 7.04 (4H, s)

EXAMPLE 18

Synthesis of 3-[2-[4-[Bis(4-fluorophenyl)methylene]-piperidin-1-yl]ethyl]-6,7,8,9-tetrahydro-2H-pyrido-[1,2-a]-1,3,5-triazine-2,4(3H)-dione Dihydrochloride In 50 mλ of methanol was dissolved 1 38 g of 3-[2-[4-[bis(4-fluorophenyl)methylene]piperidin-1-yl]ethyl]-6,7,8,9-tetrahydro-2H-pyrido[1,2-a]-1,3,5-triazine-2,4(3H)-dione obtained in Example 17, and 0.8 mλ of concentrated hydrochloric acid was added thereto, followed by concentration to dryness under reduced pressure. The residue was crystallized from a mixture of methanol and isopropanol and then recrystallized to obtain 1.03 g of the entitled compound as a colorless powder.

Melting Point: 192°–195° C.

NMR Spectrum (DMSO-d$_6$) δ: 1.7–2.0 (4H, m), 2.5–2.9 (6H, m), 3.0–3.4 (4H, m), 3.5–3.8 (4H, m), 4.19 (2H, t), 7.18 (8H, d), 9.85 (1H, s), 11.41 (1H, bs)

IR Spectrum ν (KBr) cm$^{-1}$: 3450, 2550, 1760, 1730, 1620, 1510, 1450

Elemental Analysis for $C_{27}H_{28}F_2N_4O_2 \cdot 2HC\lambda$: Calcd. (%): C 58.81; H 5.48; N 10.16. Found (%): C 58.85; H 5.74; N 10.11.

EXAMPLE 19

Synthesis of 3-[2-[4-[Bis(4-fluorophenyl)-methylene]piperidin-1-yl]ethyl]-7,8-dihydro-2H,6H,pyrrolo[1,2-a]-1,3,5-triazine-2,4(3H)-dione In the manner described in Example 17, 7,8-dihydro-2H,6H-pyrrolo[1,2-a]-1,3,5-triazine-2,4(3H)-dione obtained in Example 4-1) and 4-[bis(4-fluorophenyl)methylene]-1-(2-hydroxyethyl)piperidine were condensed in N,N-dimethylformamide in the presence of triphenylphosphine and diethyl azodicarboxylate to obtain the entitled compound as an oily substance.

NMR Spectrum (CDCλ$_3$) δ: 2.2–2.5 (6H, m), 2.5–2.8 (6H, m), 3.02 (2H, t), 4.1 (4H, m), 6.99 (8H, m)

EXAMPLE 20

Synthesis of 3-[2-[4-[Bis(4-fluorophenyl)methylene]-piperidin-1-yl]ethyl]-7,8-dihydro-2H,6H-pyrrolo[1,2-a]-1,3,5-triazine-2,4(3H)-dione Dihydrochloride In 50 mλ of methanol was dissolved 2.44 g of 3-[2-[4-[bis(4-fluorophenyl)methylene]piperidin-1-yl]ethyl]-7,8-dihydro-2H,6H-pyrrolo[1,2-a]-1,3,5-triazine-2,4(3H)-dione obtained in Example 19, and 1 mλ of concentrated hydrochloric acid was added thereto, followed by concentration to dryness under reduced pressure. The residue was crystallized from a mixture of methanol and isopropanol and then recrystallized to obtain 1.0 g of the entitled compound as a colorless powder.

Melting Point: 173°-180° C.

NMR Spectrum (DMSO-$d_6$) δ: 2.10 (2, m), 2.3–2.7 (4H, m), 2.90 (2H, t), 2.9–3.4 (4H, m), 3.5–3.8 (2H, m), 3.88 (2H, t), 4.14 (2H, t), 7.18 (8H, d), 11.22 (1H, b)

IR Spectrum ν (KBr) cm$^{-1}$: 3450, 1725, 1650, 1600, 1580, 1510, 1450, 1420, 1220

Elemental Analysis for $C_{26}H_{26}F_2N_4O_2 \cdot 2HC\lambda$: Calcd. (%): C 58.11; H 5.25; N 10.43. Found (%): C 58.06; H 5.44; N 10.63.

EXAMPLE 21

Synthesis of 3-[2-[4-[Bis(4-fluorophenyl)methylene]piperidin-1-yl]ethyl]-2H-thiazolo-[3.2-a]-1,3,5-triazine-2,4(3H)-dione Hydrochloride In 20 mλ of N,N-dimethylformamide were dissolved 1.0 g of 2H-thiazolo[3,2-a]-1,3,5-triazine-2,4(3H)-dione, 2.0 g of 1-(2-hydroxyethyl)-4-[bis(4-fluorophenyl)methylene]piperidine and 1.86 g of triphenylphosphine, and 1.25 g of diethyl azodicarboxylate was added dropwise thereto with stirring under ice-cooling. After stirring for 30 minutes, the reaction mixture was concentrated to dryness under reduced pressure. The residue was applied to a column contained with g of silica gel and eluted with 4% methanol-containing chloroform. The eluate was concentrated to dryness under reduced pressure to obtain 2.05 g of the base of the entitled compound as an oily substance. The resulting base was dissolved in 50 mλ of ethanol, and 0.5 mλ of concentrated hydrochloric acid was added thereto. The mixture was concentrated to dryness under reduced pressure. Ethanol was added to the residue, followed by concentration under reduced pressure repeatedly. The precipitated crystals were collected by filtration to obtain 1.76 g of the entitled compound as colorless crystals.

Melting Point: 251°-253° C.

NMR Spectrum (DMSO-$d_6$) δ: 2.4–2.8 (4H, m), 2.5–2.9 (4H, m), 3.6–3.8 (2H, m), 4.22 (2H, t), 7.18 (9H, m), 7.73 (1H, d), 11.2 (1H, b)

IR Spectrum ν (KBr) cm$^{-1}$: 3450, 2340, 1740, 1650, 1580, 1550, 1500, 1420

Elemental Analysis for $C_{25}H_{22}F_2N_4O_2S \cdot HC\lambda$: Calcd. (%): C 58.08; H 4.48; N 10.84. Found (%): C 57.94; H 4.63; N 10.84.

EXAMPLE 22

Synthesis of 3-[2-[4-(4-Chlorobenzoyl)-piperidinl-yl]ethyl]-6,7,8,9-tetrahydro-2H-pyrido[1,2-a]-1,3,5-triazine-2,4(3H)-dione In the manner described in Example 1–2), 6,7,8,9-tetrahydro-2H-pyrido[1,2-a]-1,3,5-triazine-2,4(3H)-dione obtained in Example 1–1) and 4-(4-chlorobenzoyl)-1-(2-hydroxyethyl)piperidine were condensed in N,N-dimethylformamide in the presence of triphenylphosphine and diethyl azodicarboxylate to obtain the entitled compound as colorless crystals.

Melting Point: 142°-144° C.

NMR Spectrum (CDC$\lambda_3$) δ: 1.6–2.1 (8H, m), 2.1–2.4 (2H, m), 2.67 (2H, t), 2.82 (2H, t), 2.9–3.2 (3H, m), 3.85 (2H, t), 4.07 (2H, t), 7.43 (2H, d), 7.86 (2H, d)

IR Spectrum ν (KBr) cm$^{-1}$: 3448, 3964, 2940, 2804, 1726, 1680, 1588

EXAMPLE 23

Synthesis of 3-[2-[4-(4-Chlorobenzoyl)piperidin-1-yl]ethyl]-6,7,8,9-tetrahydro-2H-pyrido-[1,2-a]-1.3,5-triazine-2,4(3H)-dione Hydrochloride In 30 mλ of ethanol was dissolved 1.59 g of 3-[2-[4-(4-chlorobenzoyl)piperidin-1-yl]ethyl]-6,7,8,9-tetrahydro-2H-pyrido[1,2-a]-1,3,5-triazine-2,4(3H)-dione obtained in Example 22, and 2 mλ of concentrated hydrochloric acid was added thereto, followed by concentration to dryness under reduced 1.26 g of the entitled compound as colorless crystals.

Melting Point: 273°-275° C.

IR Spectrum ν (KBr) cm$^{-1}$: 3448, 2952, 2504, 1726, 1670, 1594, 1480, 1442, 1410

Elemental Analysis for $C_{21}H_{25}C\lambda N_4O_3 \cdot HC\lambda$: Calcd. (%): C 55.63; H 5.78; N 12.36. Found (%): C 55.20; H 5.92; N 12.05.

EXAMPLE 24

Synthesis of 3-[2-Methyl-2-[4-(4-fluorobenzoyl)piperidin-1-yl]ethyl]-6,7,8,9-tetrahydro-2H-pyrido[1,2-a]-1,3,5-triazine-2,4(3H)-dione In the manner described in Example 1–2), 6,7,8,9-tetrahydro-2H-pyrido[1,2-a]-1,3,5-triazine-2,4(3H)-dione obtained in Example 1–1) and 4-(4-fluorobenzoyl)-1-(1-phenyl-2-hydroxyethyl)piperidine were condensed in N,N-dimmethylformamide in the presence of triphenylphosphine and diethyl azodicarboxylate to obtain the entitled compound as colorless crystals.

Melting Point: 151°-152° C.

NMR Spectrum (CDC$\lambda_3$) δ: 1.00 (3H, d), 1.2–2.2 (8H, m), 2.2–2.9 (5H, m), 2.9–3.4 (3H, t), 3.4–4.3 (4H, m), 7.11 (2H, m), 7.89 (2H, m)

EXAMPLE 25

Synthesis of 3-[2-Phenyl-2-[4-(4-fluorobenzoyl)piperidin-1-yl]ethyl]-6,7,8,9-tetrahydro-2H-pyrido[1,2-a]-1,3,5-triazine-2,4(3H)-dione In the manner described in Example 1–2), 6,7,8,9-tetrahydro-2H-pyrido[1,2-a]-1,3,5-triazine-2,4(3H)-dione obtained in Example 1-1) and 4-(4-fluorobenzoyl)-1-(1-phenyl-2-hydroxyethyl)piperidine were condensed in N,N-dimethylformamide in the presence of triphenylphosphine and diethyl azodicarboxylate to obtain the entitled compound as a colorless oily substance.

NMR Spectrum (CDCλ3) δ: 1.6 (1H, b), 1.66–1.84 (4H, bs), 1.9 (2H, m), 1.97 (2H, m), 2.33 (1H, b), 2.81 (2H, t), 2.90 (2H, bd), 3.0 (1H, bs), 3.24 (1H, bs), 3.82 (2H, m), 3.99 (1H, dd), 4.23 (1H, bs), 4.74 (1H, dd), 7.07 (2H, t), 7.23 (2H, d), 7.30–7.37 (3H, m), 7.86 (2H, dd)

REFERENCE EXAMPLE 1

Synthesis of 2-[2-(4-Methylbenzenesulfonyloxy)-ethyl]-1,2,4-triazolo[4,3-a]pyridin-3(2H)-one In 50 mλ of pyridine was dissolved 3.6 g of 2-(2-hydroxyethyl)-1,2,4-triazo[4,3-a]pyridin-3(2H)-one, and 7.0 g of p-toluenesulfonyl chloride was added thereto under ice-cooling, followed by stirring for 6 hours. The reaction mixture was concentrated to dryness under reduced pressure. To the residue was added diluted hydrochloric acid, and the mixture was extracted with 150 mλ of chloroform. The chloroform solution was applied to a column contained with 40 g of silica gel and eluted with chloroform to obtain 4.7 g of the entitled compound as colorless crystals.

Melting Point: 149°–151° C.

NMR Spectrum (CDCλ3) δ: 2.73 (3H, s), 4.21 (2H, t), 4.47 (2H, t), 6.48 (1H, m), 6.9–7.45 (4H, m 7.6–7.85 (3H, m)

IR Spectrum ν (KBr) cm$^{-1}$: 1720, 1650, 1360, 1195, 1180

REFERENCE EXAMPLE 2

Synthesis of 2-[2-(4-Methylbenzenesulfonyloxy)ethyl]-5,6,7,8-tetrahydro-1,2,4-triazolo[4,3-a]pyridin-3(2H)-one 1) 2-(2-Hvdroxvethvl)-5,6,7,8-tetrahvdro-1,2,4-triazolo[4,3-a]-pridin-3(2H)-one In 100 mλ of ethanol was dissolved 5.4 g of 2-(2-hydroxyethyl)-1,2,4-triazolo[4,3-a]pyridin-3(2H)-one, and 0.6 g of platinum oxide was added thereto, and the mixture was shaken in a hydrogen atmosphere. The catalyst was removed by filtration, and the filtrate was concentrated to dryness under reduced pressure to obtain 5.2 g of the entitled compound as colorless crystals.

Melting Point: 99°–100° C.

NMR Spectrum (CDCλ3) δ: 1.7–2.1 (4H, m), 2.68 (2H, t), 3.42 (1H, s), 3.62 (2H, t), 3.93 (4H, s)

IR Spectrum ν (KBr) cm$^{-1}$: 3420, 1700, 1675, 1585, 1500, 1160

2) 2-[2-(4-Methylbenzenesulfonyloxy)ethyl]-5,6,7,8-tetrahydro-1,2,4-triazolo[4,3-a]pyridin-3(2H)-one In the manner described in Reference Example 1, 2-(2-hydroxyethyl)-5,6,7,8-tetrahydro-1,2,4-triazolo[4,3-a]pyridin-3(2H)-one was tosylated to obtain the entitled compound as colorless crystals.

Melting Point: 102°–103° C.

NMR Spectrum (CDCλ3) δ: 1.7–2.1 (4H, m) 2.44 (3H, s), 2.63 (2H, t), 3.58 (2H, t), 3.98 (2H, t), 4.32 (2H, t), 7.33 (2H, d), 7.80 (2H, d)

IR Spectrum ν (KBr) cm$^{-1}$: 1720, 1705, 1605, 1580, 1500, 1370, 1200, 1085

REFERENCE EXAMPLE 3

Synthesis of 2-[2-(4-Methylbenzenesulfonyloxy)ethyl]-2,5,6,7,8,9-hexahydro-3H-1,2,4-triazolo[4,3-a]azepin-3-one 1) 2-[2-(3,4,5,6-Tetrahydro-2H-pyran-2-yloxy-ethyl]-2,5,6,7,8,9-hexahydro-3H-1,2,4-triazolo[4,3-a]azepin-3-one In 100 mλ of acetone, 3.1 g of 2,5,6,7,8,9-hexahydro-3H-triazolo[4,3-a]azepin-3-one, 4.6 g of 2-(3,4,5,6-tetrahydro-2H-pyran-2-yloxy)ethyl bromide and 6.9 g of potassium carbonate were refluxed for 20 hours. The insoluble material was removed by filtration, and the filtrate was concentrated to dryness under reduced pressure. The residue was applied to a column contained with 30 g of silica gel and eluted with chloroform to obtain 2.7 g of the entitled compound as an oily substance.

NMR Spectrum (CDCλ3) δ: 1.2–2.3 (12H, m), 2.5–2.8 (2H, m), 3.3–4.05 (8H, m), 4.6 (1H, bs)

2) 2-(2-Hydroxyethyl)-2,5,6,7,8,9-hexahydro-3H-1,2,4-triazolo-[4,3-a]azepin-3-one In 20 mλ of ethanol was dissolved 2.7 g of 2-[2-(3,4,5,6-tetrahydro-2H-pyran-2-yloxy)ethyl]-2,5,6,7,8,9-hexahydro-3H-1,2,4-triazolo[4,3-a]azepin-3-one, and 1 mλ of concentrated hydrochloric acid was added thereto, followed by stirring for 30 minutes. The reaction mixture was concentrated to dryness under reduced pressure, and isopropanol was added to the residue, followed by filtration to give 1.8 g of the entitled compound as colorless crystals.

Melting Point: 84°–86° C.

NMR (CDCl3) δ: 1.8 (6H, bs), 2.70 (2H, m), 3.20 (1H, bs), 3.77 (2H, m), 3.96 (4H, s)

IR Spectrum ν (KBr) cm$^{-1}$: 3410, 1700, 1680, 1590, 1480

3) 2-[2-(4-Methylbenzenesulfonyloxy)ethyl]-2,5,6,7,8,9-hexahydro-3H-1,2,4-triazolo4,3-a]azepin-3-one In the manner described in Reference Example 1, 2-(2-hydroxyethyl)-2,5,6,7,8,9-hexahydro-3H-1,2,4-triazolo[4,3-a]azepin-3-one was tosylated to obtain the entitled compound as an oily substance.

NMR Spectrum (CDCλ3) δ: 1.77 (6H, bs), 2.43 (3H, s), 2.62 (2H, m), 3.74 (2H, m), 4.0 (2H, m), 4.31 (2H, t), 7.39 (2H, m), 7.83 (2H, m)

REFERENCE EXAMPLE 4

Synthesis of 2-(2-Chloroethyl)-5,6,7,8-tetrahydro-1,2,4-triazolo[4,3-a]pyridin-3(2H)-one In 500 mλ of acetonitrile, 61.0 g of 5,6,7,8-tetrahydro-1,2,4-triazolo[4,3-a]pyridin-3(2H)-one, 164 g of 1-bromo-2-chloroethane and 90.8 g of anhydrous potassium carbonate were refluxed for 8 hours. The insoluble material was removed by filtration, and the filtrate was concentrated to dryness under reduced pressure. The residue was applied to a column contained with 200 g of silica gel and eluted with a 20:1 (by volume) mixture of chloroform and ethanol. After concentration of the eluate, the residue was crystallized from a mixture of isopropyl ether and ethyl ether, followed by filtration to obtain 59.8 g of the entitled compound as colorless crystals.

Melting Point: 46°–49° C.

NMR Spectrum (CDCλ₃) δ: 1.7–2.1 (4H, m), 2.68 (2H, t), 3.62 (2H, t), 3.77 (2H, t), 4.07 (2H, t)

IR Spectrum ν (KBr) cm⁻¹: 1700, 1580, 1495, 1435, 1410

REFERENCE EXAMPLE 5

Synthesis of 2-(2-Chloroethyl)-2,5,6,7,8,9-hexahydro-3H-1,2,4-triazolo[4,3-a]azepin-3-one The entitled compound was obtained as colorless crystals from 2,5,6,7,8,9-hexahydro-3H-1,2,4-triazolo[4,3-a]azepin-3-one and 1-bromo-2-chloroethane in the manner described in Reference Example 4.

Melting Point: 68°–70° C.

NMR Spectrum (CDCλ₃) δ: 1.52–2.0 (6H, m), 2.55–2.80 (2H, m), 3.62–3.95 (4H, m), 3.95–4.22 (2H, m)

IR Spectrum ν (KBr) cm⁻¹: 1700, 1580, 1480

REFERENCE EXAMPLE 6

Synthesis of 2-(2-Chloroethyl)-2,5,6,7-tetrahydro-3H-pyrrolo2,1-c]-1,2,4-triazol-3-one The entitled compound was obtained as colorless crystals from 2,5,6,7-tetrahydro-3H-pyrrolo[2,1-c]-1,2,4-triazol-3-one and 1-bromo-2-chloroethane described in Reference Example 4.

Melting Point: 91°–92° C.

NMR Spectrum (DMSO-d₆) δ: 2.3–2.58 (2H, m), 2.73 (2H, t-like), 3.64 (2H, t), 3.82–3.98 (4H, m)

IR Spectrum ν (KBr) cm⁻¹: 3450, 2970, 1700, 1600, 1480

REFERENCE EXAMPLE 7

Synthesis of 2-(2-Chloroethyl)-2,5,6,8-tetrahydro-3H-1,2,4-triazolo[3,4-c]-1,4-oxazin-3-one The entitled compound was obtained as a colorless crystalline powder from 2,5,6,8-tetrahydro-3H-1,2,4-triazolo-[3,4-c]-1,4-oxazin-3-one and 1-bromo-2-chloroethane in the same manner as in Reference Example 4.

Melting Point: 84°–86° C.

NMR Spectrum (CDCλ₃) δ: 3.65–3.84 (4H, q-like), 3.96–4.18 (4H, m), 4.64 (2H, s)

IR Spectrum ν (KBr) cm⁻¹: 3420, 2940, 1710, 1580, 1500

REFERENCE EXAMPLE 8

Synthesis of 2-(2-Chloroethyl)-6,7-dihydro-5H-1,2,4-triazolo3,4-b]-1,3-oxazin-3(2H)-one The entitled compound was obtained as colorless crystals from 6,7-dihydro-5H-1,2,4-triazolo[3,4-b]-1,3-oxazin-3(2H)-one and 1-bromo-2-chloroethane in the same manner as in Reference Example 4.

NMR Spectrum (CDCλ₃) δ: 2.16 (2H, m), 3.74 (4H, t), 4.01 (2H, dt), 4.37 (2H, t)

REFERENCE EXAMPLE 9

Synthesis of 2-(2-Chloroethyl)-2,5,6,8-tetrahydro-3H-1,2,4-triazolo3,4-c]-1,4-thiazin-3-one The entitled compound was obtained as a colorless crystalline powder from 2,5,6,8-tetrahydro-3H-1,2,4-triazolo[3,4-c]-1,4-thiazin-3-one and 1-bromo-2-chloroethane in the manner described in Reference Example 4.

Melting Point: 86°–88° C.

NMR Spectrum (CDCλ₃) δ: 2.98 (2H, t), 3.68 (2H, m), 4.10 (2H, t), 4.8 (4H, m)

EXAMPLE 26

Synthesis of 2-[2-[4-[Bis(4-fluorophenyl)methylene]piperidin-1-yl]ethyl]-5,6,7,8-tetrahydro-1,2,4-triazolo[4,3-a]pyridin-3(2H)-one 2-(2-Chloroethyl)-5,6,7,8-tetrahydro-1,2,4-triazolo[4,3-a]pyridin-3(2H)-one (26.8 g), 31.5 g of sodium iodide and 400 mλ of acetonitrile were refluxed for 30 minutes. To the reaction mixture were added 38.2 g of 4-[bis(4-fluorophenyl)methylene]piperidine and 27.6 g of potassium carbonate, followed by heating at reflux for 8 hours. The insoluble material was removed by filtration, and the filtrate was concentrated to dryness under reduced pressure. The residue was dissolved in 200 mλ of chloroform, and the solution was applied to a column contained with 550 g of silica gel and eluted with chloroform to obtain 53.0 g of the entitled compound as an oily substance.

NMR Spectrum (CDCλ₃) δ: 1.7–2.2 (4H, m), 2.2–2.9 (12H, m), 3.6 (2H, t-like), 3.92 (2H, t), 6.9–7.2 (8H, m)

EXAMPLE 27

Synthesis of 2-[2-[4-[Bis(4-fluorophenyl)methylene]piperidin-1-yl]ethyl]-5,6,7,8-tetrahydro-1,2,4-triazolo4,3-a]pyridin-3(2H)-one In 100 mλ of tetrahydrofuran were dissolved 2.0 g of -[2-(4-methylbenzenesulfonyloxy)ethyl]-5,6,7,8-tetrahydro-1,2,4-triazolo[4,3-a]pyridin-3(2H)-one, 2.8 g of 4-[bis(4-fluorophenyl)methylene]piperidine and 2 mλ of triethmylamine, and the solution was refluxed for 16 hours. The reaction mixture was concentrated to dryness under reduced pressure, and 100 mλ of water was added to the residue, followed by extraction with 100 mλ of chloroform. The chloroform solution was concentrated to dryness under reduced pressure, and the residue was applied to a column contained with 30 g of silica gel and eluted with a 20:1 (by volume) mixture of chloroform and ethanol to obtain 2.4 g of the entitled compound as an oily substance.

EXAMPLE 28

Synthesis of 2-[2-[4-[Bis(4-fluorophenyl)methylene]piperidin-1-yl]ethyl]-5,6,7,8-tetrahydro-1,2,4-triazolo[4,3-a]pyridin-3(2H)-one Hydrochloride In 200 mλ of ethanol was dissolved 53.0 g of 2-[2-[4-[bis(4-fluorophenyl)methylene]piperidin-1-yl]ethyl]-5,6,7,8-tetrahydro-1,2,4-triazolo[4,3-a]pyridin-3(2H)-one obtained in Example 26, and 20 mλ of concentrated hydrochloric acid was added to the solution. The mixture was concentrated to dryness under reduced pressure. The residue was crystallized from a small amount of ethanol, and a 1:1 (by volume) mixture of ethanol and ethyl ether was added, followed by filtration to obtain 39.5 g of the entitled compound as colorless crystals.

Melting Point: 129°–131° C.

NMR Spectrum (DMSO-$d_6$) δ: 1.07 (3H, t), 1.5–2.0 (4H, b), 2.2–2.75 (4H, m), 2.8–3.8 (10H, m), 3.43 (2H, q), 4.12 (2H, t-like), 7.14 (4H, s), 7.23 (4H, s)

IR Spectrum ν (KBr) cm$^{-1}$: 1695, 1599, 1506, 1449, 1218

Elemental Analysis for $C_{26}H_{28}F_2N_4O \cdot HCλ \cdot C_2H_6O$: Calcd. (%): C 63.09; H 6.62; N 10.51. Found (%): C 62.78; H 6.73; N 10.65.

EXAMPLE 29

Synthesis of 2-[2-[4-[Bis(4-fluorophenyl)methylene]piperidin-1-yl]ethyl]-5,6,7,8-tetrahydro-1,2,4-triazolo[4.3-a]pyridin-3(2H)-one Hydrochloride Isopropanolate In 50 mλ of isopropanol was dissolved 2.3 g of 2-[2-[4-[bis(4-fluorophenyl)methylene]piperidin-1-yl]ethyl]-5,6,7,8-tetrahydro-1,2,4-triazolo[4,3-a]pyridin-3(2H)-one obtained in Example 27, and 2 mλ of concentrated hydrochloric acid was added thereto. The mixture was concentrated to dryness under reduced pressure, and the residue was crystallized from a small amount of isopropanol. A 1:1 (by volume) mixture of isopropanol and ethyl ether was added to the crystal, followed by filtration to obtain 2.3 g of the entitled compound as colorless crystals.

Melting Point: 139°–141° C.

NMR Spectrum (DMSO-$d_6$) δ: 1.04 (6H, d), 1.6–2.0 (4H, bs), 2.2–2.75 (4H, m), 2.9–3.8 (10H, bs), 3.8 (1H, q), 4.1 (2H, t-like), 7.16 (4H, s), 7.23 (4H, s)

IR Spectrum ν (KBr) cm$^{-1}$: 1695, 1596, 1506, 1452, 1212

Elemental Analysis for $C_{26}H_{28}F_2N_4O \cdot HCλ \cdot C_3H_8O$: Calcd. (%): C 63.67; H 6.82; N 10.24. Found (%): C 63.39; H 6.59; N 10.35.

EXAMPLE 30

Synthesis of 2-[2-[4-[Bis(4-fluorophenyl)methylene]piperidin-1-yl]ethyl]-5,6,7,8-tetrahydro-1,2,4-triazolo[4,3-a]pyridin-3(2H)-one Hydrochloride 2-[2-[4-[Bis(4-fluorophenyl)methylene]piperidin-1-yl]ethyl]-5,6,7,8-tetrahydro-1,2,4-triazolo[4,3-a]pyridin-3(2H)-one hydrochloride ethanolate (39.0 g) obtained in Example 28 was recrystallized twice from a mixture of a small amount of methanol and ethyl ether to obtain 20 g of the entitled compound as colorless crystals.

Melting Point: 183°–185° C.

NMR Spectrum (DMSO-$d_6$) δ: 1.68–2.0 (4H, m), 2.3–3.8 (14H, m), 4.11 (2H, t-like), 7.18 (4H, s), 7.22 (4H, s)

NMR Spectrum (D$_2$O) δ: 1.8–2.35 (4H, b), 2.6–3.1 (6H, bm), 3.4–4.05 (8H, m), 4.38–4.65 (2H, b), 7.0–7.5 (8H, m)

IR Spectrum ν (KBr) cm$^{-1}$: 2380, 1710, 1600, 1580, 1505, 1210

Elemental Analysis for $C_{26}H_{28}F_2N_4O \cdot HCλ$: Calcd. (%): C 64.13; H 6.00; N 11.51. Found (%): C 63.85; H 6.11; N 11.44.

EXAMPLE 31

Synthesis of 2-[2-[4-[Bis(4-fluorophenyl)methylene]piperidin-1-yl]ethyl]-5,6,7,8-tetrahydro-1,2,4-triazolo4,3-a]pyridin-3(2H)-one Monomaleate In 50 mλ of ethanol was dissolved 4.5 g of 2-[2-[4-bis(4-fluorophenyl)methylene]piperidin-1-yl]ethyl]-5,6,7,8-tetrahydro-1,2,4-triazolo[4,3-a]pyridin-3(2H)-one obtained in Example 26, and 1.16 g of maleic acid was added to the solution. The mixture was concentrated to dryness under reduced pressure, and the residue was recrystallized from a mixture of ethanol and ethyl ether to obtain 4.7 g of the entitled compound as colorless crystals.

Melting Point: 144°–145° C.

NMR Spectrum (DMSO-$d_6$) δ: 1.74–2.02 (4H, m), 2.13–2.76 (4H, m), 2.86–3.63 (10H, m), 4.01 (2H, t-like), 6.08 (2H, s), 7.14 (4H, s), 7.22 (4H, s)

IR Spectrum ν (KBr) cm$^{-1}$: 1710, 1581, 1509, 1455, 1356, 1224

Elemental Analysis for $C_{26}H_{28}F_2N_4O \cdot C_4H_4O_4$: Calcd. (%): C 63.59; H 5.69; N 9.89. Found (%): C 63.47; H 5.68; N 9.70.

EXAMPLE 32

Synthesis of 2-[2-[4-[Bis(4-fluorophenyl)methylene]piperidin-1-yl]ethyl]-2,5,6,7,8,9-hexahydro-3H-1,2,4-triazolo[4,3-a]azepin-3-one In the manner described in Example 26, the entitled compound was obtained as an oily substance from 2-(2-chloroethyl)-2,5,6,7,8,9-hexahydro-3H-1,2,4-triazolo[4,3-a]-azepin-3-one and 4-[bis(4-fluorophenyl)methylene]piperidine.

NMR Spectrum (CDCλ$_3$) δ: 1.53–1.95 (6H, m), 2.2–2.47 (4H, m), 2.47–2.87 (8H, m), 3.6–3.84 (2H, m), 3.92 (2H, t), 6.9–7.2 (8H, m)

EXAMPLE 33

Synthesis of 2-[2-[4-[Bis(4-fluorophenyl)methylene]piperidin-1-yl]ethyl]-2,5,6,7,8,9-hexahydro-3H-1,2,4-triazolo[4,3-a]azepin-3-one Hydrochloride Ethanolate In 200 mλ of ethanol was dissolved 30.0 g of 2-[2-[4-[bis(4-fluorophenyl)methylene]piperidin-1-yl]ethyl-2,5,6,7,8,9-hexahydro-3H-1,2,4-triazolo[4,3-a]azepin-3-one obtained in Example 32, and 20 mλ of concentrated hydrochloric acid was added thereto. The mixture was concentrated to dryness under reduced pressure, and the residue was crystallized from a small amount of ethanol. A 1:1 (by volume) mixture of ethanol and ethyl ether was added to the crystal, followed by filtration to obtain 22.3 g of the entitled compound as colorless crystals.

Melting Point: 118°–122° C.

NMR Spectrum (DMSO-$d_6$) δ: 1.07 (3H, t), 1.4–1.95 (6H, b), 2.22–2.8 (4H, m), 2.8–4.0 (10H, m), 3.43 (2H, q), 4.15 (2H, t-like), 7.16 (4H, s), 7.24 (4H, s)

IR Spectrum ν (KBr) cm$^{-1}$: 1695, 1587, 1506, 1482, 1443, 1218

Elemental Analysis for $C_{27}H_{30}F_2N_4O \cdot HCλ \cdot C_2H_6O$: Calcd. (%): C 59.28; H 6.82; N 10.24. Found (%): C 68.95; H 6.97; N 10.01.

EXAMPLE 34

Synthesis of
2-[2-[4-[Bis(4-fluorophenyl)methylene]piperidin-1-yl]ethyl]-2,5,6,7,8,9-hexahydro-3H-1,2,4-triazolo[4,3-a]azepin-3-one Hydrochloride Hemihydrate 2-[2-[4-[Bis(4-fluorophenyl)methylene]piperidin-1-yl]ethyl]-2,5,6,7,8,9-hexahydro-3H-1,2,4-triazolo[4,3-a]azepin-3-one hydrochloride ethanolate (22 0 g) obtained in Example 33 was recrystallized twice from a mixture of a small amount of methanol and ethyl ether to obtain 17.0 g of the entitled compound as colorless crystals.

Melting Point: 119°–121° C.

NMR Spectrum (DMSO-$d_6$+$D_2O$) δ: 1.4–1.96 (6H, m), 2.2–4.0 (14H, m), 4.15 (2H, t-like), 7.18 (4H, s), 7.26 (4H, s)

IR Spectrum ν (KBr) cm$^{-1}$: 1700, 1590, 1505, 1480, 1440, 1220

Elemental Analysis for $C_{27}H_{30}F_2N_4O \cdot HCλ \cdot \frac{1}{2}H_2O$: Calcd. (%): C 63.58; H 6.33; N 10.99. Found (%): C 63.66; H 6.47; N 10.97.

EXAMPLE 35

Synthesis of
2-[2-[4-[(4-Fluorophenyl)(phenyl)methylene]piperidin-1-yl]ethyl]-2,5,6,7,8,9-hexahydro-3H-1,2,4-triazolo[4,3-a]azeoin-3-one In the manner described in Example 27, the entitled compound was obtained as an oily substance from 2-[2-(4-triazolo[methylbenzenesulfonyloxy)ethyl]-2,5,6,7,8,9-hexahydro-3H-1,2,4-triazolo[4,3-a]azepin-3-one and 4-[(4-fluorophenyl)(phenyl)-methylene]-piperidine.

NMR Spectrum (CDCλ$_3$) δ: 1.5–2.0 (6H, m), 2.28–2.9 (12H, m), 3.68–3.9 (2H, m), 3.92 (2H, t), 6.8–7.5 (9H, m)

EXAMPLE 36

Synthesis of
2-[2-[4-[(4-Fluorophenyl)(phenyl)methylene]piperidin-1-yl]ethyl]-2,5,6,7,8,9-hexahydro-3H-1,2,4-triazolo[4,3-a]azepin-3-one Hydrochloride Ethanolate In 20 mλ of ethanol was dissolved 1 9 g of 2-[2-[4-(4-fluorophenyl)(phenyl)methylene]piperidin-1-yl]ethyl]-2,5,6,7,8,9-hexahydro-3H-1,2,4-triazolo[4,3-a]azepin-3-one obtained in Example 35, and 1 mλ of hydrochloric acid was added thereto. The mixture was concentrated to dryness under reduced pressure, and the residue was crystallized from a small amount of ethanol. A 1:1 (by volume) mixture of ethanol and ethyl ether was added thereto, followed by filtration to give 1.4 g of the entitled compound as colorless crystals.

Melting Point: 118°–120° C.

NMR Spectrum (DMSO-$d_6$) δ: 1.05 (3H, t , 1.3–1.9 (6H, m), 2.2–2.8 (6H, m), 2.8–3.9 (8H, m), 3.45 (2H, q), 4.13 (2H, t-like), 7.05–7.50 (9H, m)

IR Spectrum ν (KBr) cm$^{-1}$: 1715

Elemental Analysis for $C_{27}H_{31}FN_4O \cdot HCλ \cdot C_2H_6O$: Calcd. (%): C 65.83; H 7.24; N 10.06. Found (%): C 65.52; H 7.26; N 10.25.

EXAMPLE 37

Synthesis of
2-[2-[4-(Diphenylmethylene)piperidin-1-yl]ethyl]-2,5,6,7,8,9-hexahydro-3H-1,2,4-triazolo[4,3-a]azepin-3-one Hydrochloride Ethanolate In 100 mλ of tetrahydrofuran were dissolved 3.4 g of -[2-(4-methylbenzenesulfonyloxy)ethyl]-2,5,6,7,8,9-hexahydro-3H-1,2,4-triazolo[4,3-a]azepin-3-one, 3.0 g of 4-(diphenylmethylene)piperidine and 2 mλ of triethylamine, and the solution was refluxed for 16 hours. The reaction mixture was concentrated to dryness under reduced pressure, and 100 mλ of water was added to the residue. The mixture was extracted with of chloroform, and the chloroform solution was concentrated to dryness under reduced pressure. The residue was subjected to column chromatography using 20 g of silica gel and eluted with a 20:1 (by volume) mixture of chloroform and ethanol to obtain an oily substance. The product was dissolved in 100 mλ of ethanol, and 2 mλ of concentrated hydrochloric acid was added thereto, followed by concentration to dryness under reduced pressure. The residue was crystallized from isopropanol and then recrystallized from a mixture of ethanol and ethyl ether to obtain 3.4 g of the entitled compound as colorless crystals.

Melting Point: 117°–119° C.

NMR Spectrum (CDCλ$_3$) δ: 1.06 (3H, t), 1.4–1.9 (6H, bs), 2.2–2.8 (6H, m), 2.8–3.8 (8H, m), 3.48 (2H, q), 4.13 (2H, t-like), 7.05–7.60 (10H, m)

IR Spectrum ν (KBr) cm$^{-1}$: 1705, 1590

Elemental Analysis for $C_{27}H_{32}N_4O \cdot HCλ \cdot C_2H_6O$: Calcd. (%): C 68.15; H 7.69; N 10.96. Found (%): C 67.37; H 7.48; N 11.01.

EXAMPLE 38

Synthesis of
2-[2-[4-[Bis(4-fluorophenyl)methylene]piperidin-1-yl]ethyl]-1,2,4-triazolo[4,3-a]pyridin-3(2H)-one Hydrochloride In the manner described in Example 37, the entitled compound was obtained as colorless crystals from 2-[2-(4-methylbenzenesulfonyloxy)ethyl]-1,2,4-triazolo[4,3-a]pyridin-3(2H)-one and 4-[bis(4-fluorophenyl)methylene]piperidine.

Melting Point: 127°–129° C.

NMR Spectrum (DMSO-$d_6$) δ: 2.2–3.8 (10H, m), 4.42 (2H, t-like), 6.70 (1H, m), 7.13 (4H, s), 7.30 (4H, s), 7.30 (2H, m), 7.93 (1H, d)

IR Spectrum ν (KBr) cm$^{-1}$: 1710, 1640, 1600, 1540, 1505, 1440, 1220

Elemental Analysis for $C_{26}H_{24}F_2N_4O \cdot HCλ$: Calcd. (%): C 64.66; H 5.22; N 11.60. Found (%): C 64.34; H 5.54; N 11.52 .

EXAMPLE 39

Synthesis of
2-[2-[4-[Bis(4-fluorophenyl)methylene]piperidin-1-yl]ethyl]-2,5,6,7-tetrahydro-3H-pyrrolo[2,1-c]-1,2,4-triazol-3-one In the manner described in Example 26, the entitled compound was obtained as an oily substance from 2-(2-chloroethyl)-2,5,6,7-tetrahydro-3H-pyrrolo[2,1-c]-1,2,4-triazol-3-one and 4-[bis(4-fluorophenyl)methylene]piperidine.

NMR Spectrum (CDCλ₃) δ: 2.3–3.0 (14H, m), 3.7–4.0 (4H, m), 6.9–7.2 (8H, m)

EXAMPLE 40

Synthesis of 2-[2-[4-[Bis(4-fluorophenyl)methylene]piperidin-1-yl]ethyl]-2,5,6,7-tetrahydro-3H-pyrrolo[2,1-c]-1,2,4-triazol-3-one Hydrochloride Methanolate In ethanol was dissolved 2.5 g of 2-[2-[4-[bis(4-fluorophenyl)methylene]piperidin-1-yl]ethyl]-2,5,6,7-tetrahydro-3H-pyrrolo[2,1-c]-1,2,4-triazol-3-one obtained in Example 39, and 1 mλ of concentrated hydrochloric acid was added thereto. The mixture was concentrated to dryness under reduced pressure, and the residue was crystallized from a mixture of methanol and isopropanol to obtain 1.65 g of the entitled compound as colorless crystals.

Melting Point: 123°–125° C.

NMR Spectrum (DMSO-d₆) δ: 2.8–3.4 (8H, m), 3.0–3.6 (9H, m), 3.63 (2H, t), 4.10 (2H, t-like), 7.14 (4H, s), 7.22 (4H, s), 11.4 (1H, b)

IR Spectrum ν (KBr) cm⁻¹: 3400, 2950, 2550, 1680, 1600, 1500,

Elemental Analysis for $C_{25}H_{26}F_2N_4O \cdot HC\lambda \cdot CH_4O$: Calcd. (%): C 61.84; H 6.19; N 11.09. Found (%): C 62.01; H 6.37; N 11.39.

EXAMPLE 41

Synthesis of 2-[2-[4-[Bis(4-fluorophenyl)methylene]piperidin-1-yl]ethyl]-2,5,6,8-tetrahydro-3H-1,2,4-triazolo3,4-c]-1,4-oxazin-3-one In the manner described in Example 26, the entitled compound was obtained as an oily substance from 2-(2-chloroethyl)-2,5,6,8-tetrahydro-3H-1,2,4-triazolo[3,4-c]-1,4-oxazin-3-one and 4-[bis(4-fluorophenyl)methylene]piperidine.

NMR Spectrum (CDCλ₃) δ: 2.37 (4H, m), 2.54 (4H, m), 2.72 (2H, t), 3.6–4.1 (6H, m), 4.62 (2H, s), 6.84–7.03 (8H, m)

EXAMPLE 42

Synthesis of 2-[2-[4-[Bis(4-fluorophenyl)methylene]piperidin-1-yl]ethyl]-2,5,6,8-tetrahydro-3H-1,2,4-triazolo[3,4-c]-1,4-oxazin-3-one Hydrochloride In methanol was dissolved 3.3 g of 2-[2-[4-[bis(4-fluorophenyl)methylene]piperidin-1-yl]ethyl]-2,5,6,8-tetrahydro-3H-1,2,4-triazolo[3,4-c]-1,4-oxazin-3-one obtained in Example 41, and 1 mλ of concentrated hydrochloric acid was added thereto, followed by concentration to dryness under reduced pressure. The residue was crystallized from ethanol and then recrystallized from a mixture of methanol and isopropyl alcohol to obtain 1.5 g of the entitled compound as colorless crystals.

Melting Point: 139°–144° C.

NMR Spectrum (DMSO-d₆) δ: 2.4–2.7 (4H, m), 3.0–3.5 (6H, m), 3.56 (2H, t), 3.97 (2H, t), 4.15 (2H, t), 4.62 (2H, s), 7.14 (4H, s), 7.22 (4H, s), 11.29 (1H, b)

IR Spectrum ν (KBr) cm⁻¹: 3550, 2540, 1710, 1600, 1510, 1440

Elemental Analysis for $C_{25}H_{26}F_2N_4O_2 \cdot HC\lambda$: Calcd. (%): C 61.41; H 5.56; N 11.46. Found (%): C 61.04; H 5.83; N 11.36.

EXAMPLE 43

Synthesis of 2-[2-[4-[Bis(4-fluorophenyl)methylene]piperidin-1-yl]ethyl]-6,7-dihydro-5H-1,2,4-triazolo[3,4-b]-1,3-oxazin-3(2H)-one In the manner described in Example 26, the entitled compound was obtained as an oily substance from 2-(2-chloroethyl)-6,7-dihydro-5H-1,2,4-triazolo[3,4-b]-1,3-oxazin-3(2H)-one and 4-[bis(4-fluorophenyl)methylene]piperidine.

NMR Spectrum (CDCλ₃) δ: 2.0–2.6 (10H, m), 2.70 (2H, t), 3 6–3.9 (4H, m), 4.34 (2H, m), 6.8–7.03 (8H, m)

EXAMPLE 44

Synthesis of 2-[2-[4-Bis(4-fluorophenyl)methylene]piperidin-1-yl]ethyl]-6,7-dihydro-5H-1,2,4-triazolo[3,4-b]-1,3-oxazin-3(2H)-one Hydrochloride Hemihydrate In 50 mλ of ethanol was dissolved 1.6 g of 2-[2-[4-bis(4-fluorophenyl)methylene]piperidin-1-yl]ethyl]-6,7-dihydro-5H-1,2,4-triazolo[3,4-b]-1,3-oxazin obtained in Example 43, and 0.5 mλ of concentrated hydrochloric acid was added thereto, followed by concentration to dryness under reduced pressure. The residue was crystallized from ethanol, and then recrystallized from a mixture of methanol and isopropanol to obtain 0.85 g of the entitled compound as colorless crystals.

Melting Point: 138°–139° C.

NMR Spectrum (DMSO-d₆) δ: 2.1 (2H, m), 2.5 (2H, m), 3.0–3.7 (10H, m), 4.01 (2H, t), 4.35 (2H, t), 7.13 (4H, s), 7.21 (4H, s), 10.86 (1H, b)

IR Spectrum ν (KBr) cm⁻¹: 3450, 1710, 1620, 1510

Elemental Analysis for $C_{25}H_{26}F_2N_4O_2 \cdot HC\lambda \cdot \frac{1}{2}H_2O$: Calcd. (%): C 60.30; H 5.67; N 11.25. Found (%): C 60.19; H 5.65; N 11.12.

EXAMPLE 45

Synthesis of 2-[2-[4-[Bis(4-fluorophenyl)methylene]piperidin-1-yl]ethyl]-2,5,6,8-tetrahydro-3H-1,2,4-triazolo3,4-c]-1,4-thiazin-3-one In the manner described in Example 26, the entitled compound was obtained as an oily substance from 2-(2-chloroethyl)-2,5,6,8-tetrahydro-3H-1,2,4-triazolo[3,4-c]-1,4-thiazin-3-one and 4-[bis(4-fluorophenyl)methylene]piperidine.

NMR Spectrum (CDCλ₃) δ: 2.3–2.6 (8H, m), 2.75 (2H, t), 2.97 (2H, t), 3.66 (2H, s), 3.85 (2H, t), 3.93 (2H, t), 6.96 (4H, d), 7.04 (4H, s)

EXAMPLE 46

Synthesis of 2-[2-[4-[Bis(4-fluorophenyl)methylene]piperidin-1-yl]ethyl]-2,5,6,8-tetrahydro-3H-1,2,4-triazolo[3,4-c]-1,4-thiazin-3-one Hydrochloride Hemihydrate In 50 mλ of ethanol was dissolved 2.1 g of 2-[2-[4-bis(4-fluorophenyl)methylene]piperidin-1-yl]ethyl]-2,5,6,8-tetrahydro-3H-1,2,4-triazolo[3,4-c]-1,4-thiazin-3-one obtained in Example 45, and 0.5 mλ of concentrated hydrochloric acid was added thereto, followed by concentration to dryness under reduced pressure. The residue was crystallized from isopropanol and then recrystallized from a mixture of methanol and isopropyl ether to obtain 1.73 g of the entitled compound as colorless crystals.

Melting Point: 178°–180° C.

NMR Spectrum (DMSO-d$_6$) δ: 2.9-3.8 (14H, m), 3.75 (2H, s), 4.16 (2H, t), 7.18 (8H, d), 11.2 (1H, b)

IR Spectrum ν (KBr) cm$^{-1}$: 3450, 1720, 1600, 1506

Elemental Analysis for C$_{25}$H$_{26}$F$_2$N$_4$OS·HCλ·½H$_2$O: Calcd. (%): C 58.42; H 5.49; N 10.90. Found (%): C 58.31; H 5.78; N 10.77.

EXAMPLE 47

Synthesis of 2-[2-[4-[Bis(4-methoxyphenyl)methylene]piperidin-1-yl]ethyl]-5,6,7,8-tetrahydro-1,2,4-triazolo[4,3-a]pyridin-3(2H)-one Hydrochloride Monohydrate 2-(2-Chloroethyl)-5,6,7,8-tetrahydro-1,2,4-triazolo[4,3-a]-pyridin-3(2H)-one (2.08 g), 3.1 g of sodium iodide and 100 mλ of acetonitrile were refluxed for 30 minutes, and 3.1 g of 4-[bis(4-methoxyphenyl)methylene]piperidine and 2.8 g of potassium carbonate were added thereto, followed by refluxing for 18 hours. The insoluble material was removed by filtration, and the filtrate was concentrated to dryness under reduced pressure. The residue was dissolved in 100 mλ of chloroform, and the solution was applied to a column contained with 130 g of silica gel and eluted with a 15:1 (by volume) mixture of chloroform and ethanol. The eluate was concentrated to dryness, and the resulting residue was dissolved in ethanol, of concentrated hydrochloric acid was added thereto, followed by concentration to dryness. The residue was recrystallized from a mixture of ethanol and ethyl ether to obtain 0.85 g of the entitled compound as colorless crystals.

Melting Point: 199°-203° C.

NMR Spectrum (DMSO-d$_6$) δ:1.7-2.0 (4H, m), 2.5-3.8 (14H, m), 3.8 (6H, s), 4.17 (2H, m), 6.9 (4H, d), 7.1 (4H, d)

Elemental Analysis for C$_{28}$H$_{34}$N$_4$O$_3$·HCλ·½H$_2$O: Calcd. (%): C 63.56; H 7.05; N 10.59.
(%): C 63.62; H 6.72; N 10.35.

REFERENCE EXAMPLE 10

Synthesis of 2-(3-Chloropropyl)-5,6,7,8-tetrahydro-1,2,4-triazolo[4,3-alcvridin-3(2H)-one 1)
2-[3-(3,4,5,6-Tetrahydro-2H-pyran-2-yloxy)propyl-5,6,7,8-tetrahydro-1,2,4-triazolo[4,3-a]pyridin-3(2H)-one 5,6,7,8-Tetrahydro-1,2,4-triazolo[4,3-a]pyridin-(2H)-one (4.8 g), 7.7 g of 3-(3,4,5,6-tetrahydro-2H-pyran-2-yloxy)propyl bromide and 6.9 g of anhydrous potassium carbonate were refluxed in 100 mλ of acetonitrile for 20 hours. The insoluble material was removed by filtration, and the filtrate was concentrated to dryness under reduced pressure. The residue was applied to a column contained with 30 g of silica gel and eluted with chloroform to obtain 7.7 g of the entitled compound as an oily substance.

NMR Spectrum (CDCλ$_3$); δ: 1.3-1.9 (6H, m), 1.8-2.0 (6H, m), 2.55-2.85 (2H, m), 3.3-4.1 (8H, m), 4.6 (1H, bs)

2)
2-(3-Hydroxypropyl)-5,6,7,8-tetrahydro-1,2,4-triazolo-4,3-a]pyridin-3(2H)-one In 50 mλ of ethanol was dissolved 7.7 g of 2-[3-(3,4,5,6-tetrahydro-2H-pyran-2-yloxy)propyl]-5,6,7,8,-tetrahydro-1,2,4-triazolo[4,3-a]pyridin-3(2H)-one, and 10 mλ of concentrated hydrochloric acid was added thereto, followed by stirring for 24 hours. The reaction mixture was concentrated to dryness under reduced pressure, and the residue was extracted from 100 mλ of chloroform. The chloroform solution was applied to a column contained with 30 g of silica gel and eluted with a 20:1 (by volume) mixture of chloroform and ethanol to obtain 3.0 g of the entitled compound as an oily substance.

NMR Spectrum (CDCλ$_3$) δ: 1.50-2.05 (6H, bs), 2.70 (2H, m), 3.20 (2H, bs), 3.63 (2H, t), 3.90 (2H, m), 3.98 (2H, t)

3)
2-(3-Chloropropyl)-5,6,7,8-tetrahydro-1,2,4-triazolo4,3-a]-pyridin-3(2H)-one

In 50 mλ of pyridine was dissolved 3.0 g of 2-(3-hydroxypropyl)-5,6,7,8-tetrahydro-1,2,4-triazolo[4,3-a]pyridin-3(2H)-one, and 4.3 g of p-toluenesulfonyl chloride was added thereto under ice-cooling, followed by stirring for 16 hours. The reaction mixture was concentrated to dryness under reduced pressure, and diluted hydrochloric acid was added to the residue. The mixture was extracted with 100 mλ of chloroform, and the chloroform solution was concentrated to dryness under reduced pressure. The residue was applied to a column contained with 20 g of silica gel and eluted with chloroform to obtain 1.4 g of the entitled compound as an oily substance.

NMR Spectrum (CDCλ$_3$) δ: 1.50-2.00 (4H, bs), 2.23 (2H, q), 2.68 (2H, m), 3.63 (2H, m), 3.82 (2H, m), 3.94 (2H, m)

REFERENCE EXAMPLE 11

Synthesis of 2-(3-chloropropyl)-2,5,6,7,8,9-hexahydro-3H-1,2,4-triazolo[4,3-a]azepin-3-one 1)
2-[3-(3,4,5,6-Tetrahydro-2H-pyran-2-yloxy)propyl]-2,5,6,7,8,9-hexahydro-3H-1,2,4-triazolo[4,3-a]azepin-3-one In the manner described in Reference Example 10-1), the entitled compound was obtained as an oily substance from 2,5,6,7,8,9-hexahydro-3H-1,2,4-triazolo[4,3-a]azepin-3-one and 3-(3,4,5,6-tetrahydropyran-2-yloxy)propyl bromide.

2)
2-(3-Hydroxypopyl)-2,5,6,7,8,9-hexahydro-3H-1,2,4-triazolo[4,3-a]azepin-3-one In the manner described in Reference Example 10-2), 2-[3-(3,4,5,6-tetrahydro-2H-pyran-2-yloxy)propyl]-2,5,6,7,8,9-hexahydro-3H-1,2,4-triazolo[4,3-a]azepin-3-one was treated with an acid to obtain the entitled compound as colorless crystals.

Melting Point: 62°-64° C.

NMR Spectrum (CDCλ$_3$) δ:1.50-2.05 (8H, bs), 2.70 (2H, m), 3.20 (1H, bs), 3.63 (2H, t), 3.90 (2H, m), 3.98 (2H, t)

IR Spectrum ν (KBr) cm$^{-1}$: 3435, 1700, 1685, 1590, 1490, 1450, 1405

3)
2-(3-Chloropropyl)-2,5,6,7,8,9-hexahydro-3H-1,2,4-triazolo[4,3-a]azepin-3-one In the manner described in Reference Example 10-3), 2-(3-hydroxypropyl)-2,5,6,7,8,9-hexahydro-3H-1,2,4-triazolo-[4,3-a]azepin-3-one was treated with p- toluenesulfonyl chloride to obtain the entitled compound as an oily substance.

NMR Spectrum (CDCl$_3$) δ: 1.50–2.00 (6H, bs), 2.23 (2H, q), 2.68 (2H, m), 3.63 (2H, m), 3.82 (2H, m), 3.94 (2H, m)

REFERENCE EXAMPLE 12

Synthesis of 4-(2-Fluoro-4-morpholinobenzoyl)piperidine Hydrochloride Hydrochloride In 30 mλ of N,N-dimethylformamide were suspended 2.30 g of 1-acetyl-4-(2,4-difluorobenzoyl)piperidine, 0.9 mλ of morpholine and anhydrous potassium carbonate, and the suspension was heated at 80° C. for 4 days with stirring. The reaction mixture was concentrated to dryness under reduced pressure, and 100 mλ of water was added to the residue. The mixture was extracted with 100 mλ of chloroform. The chloroform solution was dried over anhydrous sodium sulfate. The solution was concentrated to dryness under reduced pressure, and the resulting oily substance was applied to a column contained with 50 g of silica gel and eluted with a 20:1 (by volume) mixture of chloroform and ethanol to obtain 2.63 g of a mixture of 1-acetyl-4-(4-fluoro-2-morpholinobenzoyl)-piperidine and 1-acetyl-4-(2-fluoro-4-morpholinobenzoyl)-piperidine as a pale yellow oily substance.

To the product was added 20 mλ of concentrated hydrochloric acid, followed by refluxing for 16 hours. The reaction mixture was extracted with 100 mλ of chloroform, and the aqueous layer was separated. After the aqueous layer was made basic with potassium carbonate, the mixture was extracted with 100 mλ of chloroform, and the chloroform solution was dried sodium sulfate. The solution was concentrated to dryness under reduced pressure, and the residue was dissolved in 50 mλ of ethanol. To the solution was added 2 mλ of concentrated hydrochloric acid followed by concentration to dryness under reduced pressure. An adequate amount of ethanol was added to the residue which was crystallized to obtain 0.6 g of the entitled compound as colorless crystals.

Melting Point: 255° C.

NMR Spectrum (DMSO-d$_6$) δ: 1.56–2.13 (4H, m), 2.72–3.57 (9H, m), 3.66–3.93 (4H, m), 6.69–7.08 (2H, m), 7.72 (1H, t)

IR Spectrum ν (KBr) cm$^{-1}$: 3410, 2950, 2920, 2790, 2710, 2640, 2500, 1680, 1620, 1520

REFERENCE EXAMPLE 13

Synthesis of 4-(4-Fluoro-2-morpholinobenzoyl)piperidine Hydrochloride

After filtration of 4-(2-fluoro-4-morpholinobenzoyl)-piperidine hydrochloride in Reference Example 12, the mother liquor was concentrated to dryness under reduced pressure, and the residue was crystallized from a mixture of ethanol and acetone to obtain 1.44 g of the entitled compound.

Melting Point: 177°–181° C.

NMR Spectrum (DMSO-d$_6$) δ: 1.59–2.06 (4H, m), 2.71–3.42 (9H, m), 3.62–3.94 (4H, m), 6.76–7.15 (2H, m), 7.35 (1H, dd)

IR Spectrum ν (KBr) cm$^{-1}$: 3450, 2920, 2820, 2710, 2480, 1655, 1615, 1550

EXAMPLE 48

Synthesis of 2-[2-[4-(4-Fluorobenzoyl)piperidin-1-yl]ethyl]-1,2,4-triazolo[4,3-a]pyridin-3-one In 100 mλ of tetrahydrofuran were dissolved 3.3 g of 2-[2(4-methylbenzenesulfonyloxy)ethyl]-1,2,4-triazolo[4,3-a]pyridin-3(2H)-one, 2.8 g of 4-(4-fluorobenzoylpiperidine and 3 mλ of triethylamine, and the solution was refluxed for 24 hours. The reaction mixture was concentrated to dryness under reduced pressure, and to the residue was added 100 mλ of water, followed by extracting with 100 mλ of chloroform. The chloroform solution was applied to a column contained with 40 g of silica gel and eluted with a 20:1 (by volume) mixture of chlorofom and ethanol to obtain 1.9 g of the entitled compound as pale yellow crystals.

Melting Point: 118°–119° C.

NMR Spectrum (CDCl$_3$) δ: 1.6–2.0 (4H, m), 2.0–2.4 (2H, m), 2.82 (2H, t), 2.85–3.3 (3H, m), 4.10 (2H, t), 6.43 (1H, m), 5.90–7.25 (4H, m), 7.6–8.04 (3H, m)

IR Spectrum ν (KBr) cm$^{-1}$: 1710, 1680, 1600, 1545

EXAMPLE 49

Synthesis of 2-[2-[4-(4-Fluorobenzoyl)piperidin-1-yl]ethyl]-1,2,4-triazolo[4,3-a]-pyridin-3(2H)-one Hydrochloride Hemihydrate In 30 mλ of methanol was dissoled 1.8 g of 2-[2-[4-(4-Fluorobenzoyl)piperidin-1-yl]ethyl]-1,2,4-triazolo[4,3-a]-pyridin-3(2H)-one obtained in Example 48, and 1 mλ of concentrated hydrochloric acid was added thereto. The mixture was concentrated to dryness under reduced pressure, and the residue was recrystallized from a mixture of methanol and ethyl ether to obtain 1.2 g of the entitled compound as pale yellow crystals.

Melting Point: 225°–237° C.

NMR Spectrum (DMSO-d$_6$) δ: 1.8–2.2 (4H, bm), 2.9–4.0 (7H, m), 4.42 (2H, t-like), 6.65 (1H, m), 7.2–7.6 (4H, t), 7.8–8.25 (3H, m)

IR Spectrum ν (KBr) cm$^{-1}$: 1710, 1670, 1640, 1600, 1545, 1445

Elemental Analysis for $C_{20}H_{21}FN_4O_2 \cdot HCl \cdot \frac{1}{2}H_2O$: Calcd. (%): C 58.04; H 5.60; N 13.54. Found (%): C 57.79; H 5.56; N 13.41.

EXAMPLE 50

Synthesis of 2-[2-[4-(4-Fluorobenzoyl)piperidin-1-yl]ethyl]-5,6,7,8-tetrahydro-1,2,4-triazolo[4,3-a]-pyridin-3(2H)-one In the manner described in Example 48, the entitled compound was obtained as pale yellow crystals from 2-[2-[4-(4-Fluorobenzoyl)piperidin-1-yl]ethyl]-5,6,7,8-tetrahydro-1,2,4-triazolo[4,3-a]-pyridin-3(2H)-one and 4-(4-fluorobenzoyl)piperidine.

Melting Point: 105°–106° C.

NMR Spectrum (CDCl$_3$) δ: 1.6–2.05 (8H, m), 2.05–2.52 (2H, m), 2.53–2.90 (4H, m), 2.9–3.4 (3H, m), 3.4–3.75 (2H, m), 3.93 (2H, t), 7.22 (2H, t), 8.03 (2H, dd)

IR Spectrum ν (KBr) cm$^{-1}$: 1705, 1685, 1600, 1575, 1500

EXAMPLE 51

Synthesis of
2-[2-[4-(4-Fluorobenzoyl)piperidin-1-yl]ethyl]-5,6,7,8-tetrahydro-1,2,4-triazolo[4,3-a]-pyridin-3(2H)-one Hydrochloride In 100 mλ of ethanol was dissolved a 3.5 g of Synthesis of 2-[2-[4-(4-Fluorobenzoyl)piperidin-1-yl]ethyl]-5,6,7,8-tetrahydro-1,2,4-triazolo[4,3-a]-pyridin-3(2H)-one obtained in Example 50, and 2 mλ of concentrated hydrochloric acid was added thereto. The mixture was concentrated to dryness under reduced pressure, and the residue was crystallized from acetone to obtain 3.2 g of the entitled compound as colorless crystals.

Melting Point: 217°–219° C.
NMR Spectrum (CDClλ$_3$) δ: 1.6–2.4 (8H, m), 2.4–2.8 (2H, m), 2.8–4.0 (11H, m), 7.25–7.57 (2H, m), 7.95–8.25 (2H, m)
IR Spectrum ν (KBr) cm$^{-1}$: 1695, 1598, 1225
Elemental Analysis for $C_{20}H_{25}FN_4O_2 \cdot HCl$: Calcd. (%): C 58.75; H 6.41; N 13.70. Found (%): C 58.67; H 6.42; N 13.63.

EXAMPLE 52

Synthesis of
2-[2-[4-(4-Fluorobenzoyl)piperidin-1-yl]propyl]-5,6,7,8-tetrahydro-1,2,4-triazolo[4,3-a]-pyridin-3(2H)-one 2-(3-Chloropopyl)-5,6,7,8-tetrahydro-1,2,4-triazolo[4,3-a]-pyridin-3(2H)-one (1.4 g) and 3 g of sodium iodie were refluxed in 100 mλ of tetrahydrofuran for 20 minutes. to the reaction mixture were added 2.1 g of 4-(4-fluorobenzoyl)piperidine and 2 mλ of triethylamine, followed by refluxing for 8 hours. The reaction mixture was concentrated to dryness under reduced pressure, and the residue was applied to a column contained with 30 g of silica gel and eluted with a 20:1 (by volume) mixture of chloroform and ethanol. The resulting oily substance was crystallized from isopropyl ether to obtain 1.2 g of the entitled compound as pale yellow crystals.

Melting Point: 136°–137° C.
NMR Spectrum (CDClλ$_3$) δ: 1.6–2.3 (12H, m), 2.34–2.59 (2H, m), 2.59–2.8 (2H, m), 2.8–3.18 (2H, m), 3.18–3.4 (1H, m), 3.4–3.7 (2H, m), 3.7–3.94 (2H, t), 7.20 (2H, t), 8.03 (2H, dd)
IR Spectrum ν (KBr) cm$^{-1}$: 1695, 1670, 1595, 1590, 1500, 1450, 1410

EXAMPLE 53

Synthesis of
2-[3-[4-(4-Fluorobenzoyl)piperidin-1-yl]propyl]-5,6,7,8-tetrahydro-1,2,4-triazolo[4,3-a]-pyridin-3(2H)-one Hydrochloride Hemihydrate In 50 mλ of ethanol was dissoled 1.1 g of 2-[3-[4-(4-Fluorobenzoyl)piperidin-1-yl]propyl]-5,6,7,8-tetrahydro-1,2,4-triazolo[4,3-a]-pyridin-3(2H)-one obtained in Example 52, and 1 mλ of concentrated hydrochloric acid was added thereto. The mixture was concentrated to dryness under reduced pressure, and the residue was crystallized from acetone to obtain 1.0 g of the entitled compound as colorless crystals.

Melting Point: 209°–211° C.
NMR Spectrum (CDCl-d$_6$) δ: 1.5–2.2 (10H, m), 2.44–2.7 (2H, m), 2.8–3.9 (9H, m), 4.13 (2H, t-like), 7.22–7.60 (2H, m), 7.9–7.22 (2H, m)
IR Spectrum ν (KBr) cm$^{-1}$: 1690, 1595, 1580
Elemental Analysis for $C_{21}H_{27}FN_4O_2 \cdot HCl \cdot \frac{1}{2}H_2O$: Calcd. (%): C 58.36; H 6.77; N 12.97. Found (%): C 58.56; H 6.91; N 12.75.

EXAMPLE 54

Synthesis of
2-[2-[4-(4-Fluorobenzoyl)piperidin-1-yl]ethyl-2,5,6,7,8,9-hexahydro-3H-1,2,4-triazolo[4,3-a]azepin-3-one In the manner described in Example 48, the entitled compound was obtained as an oily substance from 2-[2-[4-(4-Fluorobenzoyl)piperidin-1-yl]ethyl-2,5,6,7,8,9-hexahydro-3H-1,2,4-triazolo[4,3-a]azepin-3-one and 4-(4-fluorobenzoyl)piperidine.

NMR Spectrum (CDClλ$_3$) δ: 1.75 (10H, bs), 2.0–2.4 (2H, m), 2.5–2.75 (4H, m), 2.9–3.3 (3H, m), 2.77 (2H, t), 3.90 (2H, t), 7.0–7.45 (2H, m), 7.8–8.1 (2H, m)

EXAMPLE 55

Synthesis of
2-[2-[4-(4-Fluorobenzoyl)piperidin-1-yl]ethyl-2,5,6,7,8,9-hexahydro-3H-1,2,4-triazolo[4,3-a]azepin-3-one Hydrochloride In 50 mλ of ethanol was dissolved 1.1 g of 2-[2-[4-(4-Fluorobenzoyl)piperidin-1-yl]ethyl-2,5,6,7,8,9-hexahydro-3H-1,2,4-triazolo[4,3-a]azepin-3-one obtained in Example 54, and 1 mλ of concentrated hydrochloric acid was added thereto. The mixture was concentrated to dryness under reduced pressure, and the residue was crystallized from acetone to obtain 0.9 g of the entitled compound as colorless crystals.

Melting Point: 229°–231° C. NMR Spectrum (DMSO-d$_6$) δ: 1.4–1.85 (6H, m), 1.85–2.2 (4H, m), 2.57–2.8 (2H, m), 2.9–4.0 (9H, m), 4.14 (2H, t-like), 7.25–7.6 (2H, m), 7.96–8.25 (2H, m)
IR Spectrum ν (KBr) cm$^{-1}$: 1695, 1597, 1580
Elemental Analysis for $C_{21}H_{27}FN_4O_2 \cdot HCl$: Calcd. (%): C 59.64; H 6.44; N 13.25. Found (%): C 59.82; H 6.74; N 13.01.

EXAMPLE 56

Synthesis of
2-[3-[4-(4-Fluorobenzoyl)piperidin-1-yl]propyl]-2,5,6,7,8,9-hexahydro-3H-1,2,4-triazolo[4,3-a]azepin-3-one In the manner described in Example 52, the entitled compound was obtained as an oily substance from 2-(3-chloropropyl)-2,5,6,7,8,9-hexahydro-3H-1,2,4-triazolo[4,3-a]azepin-3-one and 4-(4-fluorobenzoyl)-piperidine.

NMR Spectrum (CDClλ$_3$) δ: 1.55 (12H, m), 2.5 (2H, t), 2.0–3.3 (5H, m), 2.6–2.8 (2H, m), 3.6–3.95 (4H, m), 7.0–7.35 (2H, m), 7.8–8 1 (2H, m)

EXAMPLE 57

Synthesis of
2-[3-[4-(4-Fluorobenzoyl)piperidin-1-yl]propyl]-2,5,6,7,8,9-hexahydro-3H-2,4-triazolo[4,3-a]azepin-3-one Hydrochloride In 50 mλ of ethanol was dissolved 0.7 g of 2-[3-[4-(4-fluorobenzoyl)piperidin-1-yl]propyl]-2,5,6,7,8,9-hexahydro-3H-1,2,4-triazolo[4,3-a]azepin-3-one obtained in Example 56, and 1 mλ of concentrated hydrochloric acid was added thereto. The mixture was concentrated to dryness under reduced pressure, and the residue was crystallized from acetone to obtain 0.45 g of the entitled compound as colorless crystals.

Melting Point: 213°–215° C.

NMR Spectrum (DMSO-d$_6$) δ: 1.1–1.82 (6H, m), 1.82–2.4 (6H, m), 2.5–2.8 (2H, m), 2.8–4.0 (11H, m), 7.0–7.6 (2H, m), 7.8–8.4 (2H, m)

IR Spectrum ν (KBr) cm$^{-1}$: 1700, 1680, 1595, 1580

Elemental Analysis for $C_{22}H_{29}FN_4O_2 \cdot HCλ$: Calcd. (%): C 60.47; H 6.92; N 12.82. Found (%): C 60.57; H 6 86; N 12.67.

EXAMPLE 58

Synthesis of 2-[2-[4-(4-Fluorobenzoyl)piperidin-1-yl]ethyl]-2,5,6,7-tetrahydro-3H-pyrrolo[2,1-c]-1,2,4-triazol-3-one Hydrochloride In the manner described in Example 52, the entitled compound was obtained as an oily substance from 2-(2-chloroethyl)-2,5,6,7-tetrahydro-3H-pyrrolo[2,1-c]-1,24-triazol-3-one and 4-(4-fluorobenzoyl)piperidine. The product was dissolved in 50 mλ of ethanol, and 1 mλ of concentrated hydrochloric acid was added thereto. The mixture was concentrated to dryness under reduced pressure, and the residue was recrystallized from a mixture of ethanol and isopropyl ether to obtain 0.65 g of the entitled compound as a colorless powder Melting Point: 215°–217° C.

NMR Spectrum (DMSO-d$_6$) δ: 1.8–2.2 (4H, m), 2.3–2.5 (2H, m), 2.66 (2H, t-like), 3.0–3.7 (7H, m), 3.64 (2H, t), 4.10 (2H, t), 7.38 (2H, t), 8.10 (2H, dd)

IR Spectrum ν (KBr) cm$^{-1}$: 3450, 2450, 1700, 1600

Elemental Analysis for $C_{19}H_{23}FN_4O_2 \cdot HCλ$: Calcd. (%): C 57.79; H 6.13; N 14.19. Found (%): C 57.87; H 6.43; N 13.85.

EXAMPLE 59

Synthesis of 2-[2-[4-(4-Fluorobenzoyl)piperidin-1-yl]ethyl]-6,7-dihydro-5H-1,2,4-triazolo[3,4-b]-1,3-oxazin-3(2H)-one In the manner described in Example 52, the entitled compound was obtained as an oily substance from 2-(2-chloroethyl)-6,7-dihydro-5H-1,2,4-triazolo[3,4-b]-3(2H)-one and 4-(4-fluorobenzoyl)piperidine.

NMR Spectrum (CDCλ$_3$) δ: 1.7–2.4 (8H, m), 2.72 (2H, t), 3.0–3.2 (3H, m), 3.72 (2H, t), 3.84 (2H, t), 4.36 (2H, t), 7.13 (2H, t), 7.96 (2H, dd)

EXAMPLE 60

Synthesis of 2-[2-[4-(4-Fluorobenzoyl)piperidin-1-yl]ethyl]-2,5,6,8-tetrahydro-3H-1,2,4-triazolo[3,4-c]-1,4-oxazin-3-one In the manner described in Example 52, the entitled compound was obtained as colorless crystals from 2-(2-chloroethyl)-2,5,6,8-tetrahydro-3H-1,2,4-triazolo[3,4-b]-1,4-oxazin-3-one and 4-(4-fluorobenzoyl)piperidine.

Melting Point: 127°–129° C.

NMR Spectrum (CDCλ$_3$) δ: 1.7–1.9 (4H, m), 2.0–2.4 (2H, m), 2.74 (2H, t), 2.9–3.2 (3H, m), 3.69 (2H, t), 3.85–4.07 (4H, m), 4.64 (2H, s), 7.13 (2H, t), 7.96 (2H, dd)

EXAMPLE 61

Synthesis of 2-[2-[4-(4-Fluorobenzoyl)piperidin-1-yl]ethyl]-2,5,6,8-tetrahydro-3H-1,2,4-triazolo-[3,4-c]-1,4-oxazin-3-one Hydrochloride Hemihydrate In 50 mλ of ethanol was dissolved 1.64 g of 2-[2-[4-(4-fluorobenzoyl)piperidin-1-yl]ethyl]-2,5,6,8-tetrahydro-3H-1,2,4-triazolo[3,4-c]-1,4-oxazin-3-one obtained in Example 60, of concentrated hydrochloric acid was added thereto. The mixture was concentrated to dryness under reduced pressure. The residue was crystallized from ethanol to obtain 1.37 g of the entitled compound as colorless crystals.

Melting Point: 236°–239° C.

NMR Spectrum (DMSO-d$_6$) δ: 1.8–2.2 (4H, m), 3.0–3.9 (9H, m), 3.98 (2H, t), 4.17 (2H, t), 4.63 (2H, s), 7.38 (2H, t), 8.10 (2H, dd), 11.0 (1H, bs)

IR Spectrum ν (KBr) cm$^{-1}$: 3450, 2520, 1690, 1600, 1490, 1440,

Elemental Analysis for $C_{19}H_{23}FN_4O_3 \cdot HCλ \cdot \frac{1}{2}H_2O$: Calcd. (%): C 54.35; H 6.00; N 13.34. Found (%): C 54.46; H 6.25; N 13.18.

EXAMPLE 62

Synthesis of 2-[2-[4-(4-Fluorobenzoyl)-4-hydroxypiperidin-1-yl]ethyl]-5,6,7,8-tetrahydro-1,2,4-triazolo[4,3-a]pyridin-3(2H)-one In the manner described in Example 52, the entitled compound was obtained as pale yellow crystals from 2-(2-chloroethyl)-5,6,7,8-tetrahydro-1,2,4-triazolo[4,3-a]pyridin-3(2H)-one and 4-(4-fluorobenzoyl)-4-hydroxypiperidine.

Melting Point: 165°–167° C.

NMR Spectrum (CDCλ$_3$) δ: 1.58–2.07 (4H, m), 2.07–3.0 (12H, m), 3.58 (2H, m), 3.80 (1H, s), 3.92 (2H, t), 7.11 (2H, t), 8.07–8.30 (2H, m)

IR Spectrum ν (KBr) cm$^{-1}$: 1665, 1590, 1490

EXAMPLE 63

Synthesis of 2-[2-[4-(4-Fluorobenzoyl)-4-hydroxypiperidin-1-yl]ethyl]-5,6,7,8-tetrahydro-1,2,4-triazolo[4,3-a]pyridin-3(2H)-one Hydrochloride In 50 mλ of ethanol was dissolved 2.2 g of 2-[2-[4-(4-fluorobenzoyl)-4-hydroxypiperidin-1-yl]ethyl]-5,6,7,8-tetrahydro-1,2,4-triazolo[4,3-a]pyridin-3(2H)-one obtained in Example 62, and 1 mλ of concentrated hydrochloric acid was added thereto. The mixture was concentrated to dryness under reduced pressure, and the residue was recrystallized from a mixture of ethanol and ethyl ether to obtain 1.8 g of the entitled compound as colorless crystals.

Melting Point: 202°–204° C.

NMR Spectrum (DMSO-d$_6$) δ: 1.55–2.0 (4H, m), 2.0–2.4 (4H, m), 2.55 (2H, m), 2.9–3.7 (8H, m), 4.12 (2H, t), 7.35 (2H, t), 8.29 (2H, dd)

IR Spectrum ν (KBr) cm$^{-1}$: 1715, 1685, 1600, 1500, 1440, 1260, 1240, 1150

Elemental Analysis for $C_{20}H_{25}FN_4O_3 \cdot HCλ$: Calcd. (%): C 56.53; H 5.93; N 13.19. Found (%): C 56.26; H 6.33; N 13.47.

EXAMPLE 64

Synthesis of
2-[2-[4-(4-Fluorobenzoyl)-4-hydroxypiperidin-1-yl]ethyl]-2,5,6,7,8,9-hexahydro-3H-1,2,4-triazolo[4,3-a]azepin-3-one In the manner described in Example 52, the entitled compound was obtained as pale yellow crystals from 2-(2-chloroethyl)-2,5,6,7,8,9-hexahydro-3H-1,2,4-triazolo[4,3-a]azepin-3-one and 4-(4-fluorobenzoyl)-4-hydroxypiperidine.

Melting Point: 156°–158° C.

NMR Spectrum (CDCλ$_3$) δ: 1.55–2.05 (4H, m), 2.07–3.0 (12H, m), 3.78 (2H, m), 3.90 (1H, s), 3.92 (2H, t), 7.12 (2H, t), 8.1–8.32 (2H, m)

IR Spectrum ν (KBr) cm$^{-1}$: 1680, 1595

EXAMPLE 65

Synthesis of
2-[2-[4-(4-Fluorobenzoyl)-4-hydroxypiperidin-1-yl]ethyl]-2,5,6,7,8,9-hexahydro-3H-1,2,4-triazolo[4,3-a]azepin-3-one Hydrochloride In 50 mλ of ethanol was dissolved 2.6 g of 2-[2-[4-(4-fluorobenzoyl)-4-hydroxypiperidin-1-yl]ethyl]-2,5,6,7,8,9-hexahydro-3H-1,2,4-triazolo[4,3-a]azapin-3-one obtained in Example 64, and 1 mλ of concentrated hydrochloric acid was added thereto. The mixture was concentrated to dryness under reduced pressure, and the residue was crystallized from ethyl ether, followed by recrystallization from a mixture of ethanol and ethyl ether to give 2.2 g of the entitled compound as colorless crystals.

Melting Point: 195°–197° C.

NMR Spectrum (DMSO-d$_6$) δ: 1.70 6H, bs), 1.8–2.4 (4H, m), 2.60 (2H, m), 3.0–3.8 (8H, m), 4.10 (2H, t), 7.33 (2H, t), 8.28 (2H, dd)

IR Spectrum ν (KBr) cm$^{-1}$: 1705, 1605, 1515, 1490, 1445, 1420, 1220, 1165

Elemental Analysis for $C_{21}H_{27}FN_4O_3 \cdot HC\lambda$: Calcd. (%): C 57 46; H 6.43; N 12.76. Found (%): C 57.24; H 6.56; N 12.50.

EXAMPLE 66

Synthesis of
2-[2-[trans-3-(4-Fluorophenyl)-4-(4-fluorobenzoyl)-piperidin-1-yl]ethyl]-5,6,7,8-tetrahydro-1,2,4-triazolo[4,3-a]pyridin-3(2H)-one In the manner described in Example 52, the entitled compound was obtained as an oily substance from 2-(2-chloroethyl)-5,6,7,8-tetrahydro-1,2,4-triazolo[4,3-a]pyridin-3(2H)-one and trans-3-(4-fluorophenyl)-4-(4-fluorobenzoyl)piperidine.

500 MHz-NMR Spectrum (CDCλ$_3$) δ: 1.77–1.88 (3H, m), 1.89–2.0 (3H, m), 2.28 (1H, t), 2.3 (1H, t), 2.67 (2H, t, 2.79 (2H, t), 3.08 (1H, dd), 3.15 (1H, bd), 3.35 (1H, dt), 3.55 (1H, dt), 3.61 (2H, dt), 3.91 (2H, dt), 6.86 (2H, t), 7.04 (2H, t), 7.16 (2H, m), 7.81 (2H, m)

EXAMPLE 67

Synthesis of
2-[2-[trans-3-(4-Fluorophenyl)-4-(4-fluorobenzoyl)-piperidin-1-yl]ethyl]-5,6,7,8-tetrahydro-3H-1,2,4-triazolo[4,3-a]pyridin-3(2H)-one Maleate In 50 mλ of ethanol was dissolved 0.65 g of 2-[2-trans-3-(4-fluorophenyl)-4-(4-fluorobenzoyl)piperidin-1-yl]ethyl]-5,6,7,8-tetrahydro-1,2,4-triazolo[4,3-a]pyridin-3(2H)-one obtained in Example 66, and 0.16 g of maleic acid was added thereto. The mixture was concentrated to dryness under reduced pressure, and the residue was crystallized from water to obtain 0.45 g of the entitled compound as pale yellow crystals.

Melting Point: 90°–95° C.

NMR Spectrum (DMSO-d$_6$) δ: 1.5–1.95 (4H, bs), 2.10 (2H, m), 2.60 (2H, m), 2.8–3.75 (9H, m), 4.03 (2H, t-like), 4.23 (1H, m), 6.11 (2H, s), 6.92 (6H, m), 7.85–8.14 (2H, m)

IR Spectrum ν (KBr) cm$^{-1}$: 1700, 1600, 1515, 1360, 1225

Elemental Analysis for $C_{26}H_{28}F_2N_4O_2 \cdot C_4H_4O_4$: Calcd. (%): C 61.85; H 5.54; N 9.62. Found (%): C 61.50; H 5.40; N 9.58.

EXAMPLE 68

Synthesis of
2-[2-[4-(2,4-Difluorobenzoyl)piperidin-1-yl]ethyl]-5,6,7,8-tetrahydro-1,2,4-triazolo[4,3-a]pyridin-3(2H)-one In the manner described in Example 52, the entitled compound was obtained as colorless crystals from 2-(2-chloroethyl)-5,6,7,8-tetrahydro-1,2,4-triazolo[4,3-a]-pyridin-3(2H)-one and 4-(2,4-difluorobenzoyl)piperidine.

NMR Spectrum (CDCλ$_3$) δ: 1.47–2.42 10H, m), 2.50–3.26 (7H, m), 3.6 (2H, t), 3.9 (2H, t), 6.67–7.09 (2H, m), 7.68–8.04 (1H, m)

The above crystals were dissolved in ethanol, and concentrated hydrochloric acid was added thereto. The mixture was concentrated to dryness under reduced pressure, and the residue was crystallized from a mixture of acetone and isopropyl ether, followed by recrystallization from a mixture of ethanol and isopropyl ether to yield the hydrochloride hemihydrate of the entitled compound as colorless crystals.

Melting Point: 89° C. (decomposition)

NMR Spectrum (DMSO-d$_6$) δ: 1.56–2.24 (10H, m), 2.44–3.88 (9H, m), 4.10 (2H, t), 7.15–7.60 (2H, m), 7.78–8.09 (1H, m)

IR Spectrum ν (KBr) cm$^{-1}$: 3440, 2950, 2530, 1695, 1610, 1495

Elemental Analysis for $C_{20}H_{24}F_2N_4O_2 \cdot HC\lambda \cdot \frac{1}{2}H_2O$: Calcd. (%): C 55.11; H 6.01; N 12.85. Found (%): C 55.67; H 6.38; N 12.57.

EXAMPLE 69

Synthesis of
2-[2-[4-(4-Fluoro-2-morpholinobenzoyl)piperidin-1-yl]ethyl]-5,6,7,8-tetrahydro-1,2,4-triazolo[4,3-a]pyridin-3(2H)-one In the manner described in Example 48, the entitled compound was obtained as a pale yellow oily substance from 2-[-(4-methylbenzenesulfonyloxy)ethyl]-5,6,7,8-tetrahydro-1,2,4-triazolo[4,3-a]pyridin-3(2H)-one and 4-(4-fluoro-2-morpholinobenzoyl)piperidine.

NMR Spectrum (CDCl$_3$) δ: 1.48–2.30 (11H, m), 2.63–2.79 (4H, m), 2.91–3.01 (6H, m), 3.22–3.94 (6H, m), 3.60 (2H, t), 6.66–6.86 (2H, m), 7.26 (1H, dd)

EXAMPLE 70

Synthesis of
2-[2-[4-(4-Fluoro-2-morpholinobenzoyl)piperidin-1-yl]ethyl]-5,6,7,8-tetrahydo-1,2,4-triazolo-[4,3-a]pyridin-3(2H)-one Hydrochloride Hemihydrate In 50 mλ of methanol was dissolved 0.9 g of 2-[2-[4-(4-fluoro-2-morpholinobenzoyl)piperidin-1-yl]ethyl]-5,6,7,8-tetrahydro-1,2,4-triazolo[4,3-a]pyridin-3(2H)-one obtained in Example 69, and 1 mλ of concentrated hydrochloric acid was added thereto. The mixture was concentrated to dryness under reduced pressure, and the resulting crystal was recrystallized from a mixture of methanol and isopropyl ether to obtain 0.53 g of the entitled compound as colorless crystals.

Melting Point: 159°–160° C.

NMR Spectrum (DMSO-$d_6$) δ: 1.56–2.10 (11H, m), 2.77–3.04 (4H, m), 3.22–3.89 (12H, m), 4.09 (2H, t), 6.77–7.14 (2H, m), 7.24–7.46 (1H, m)

IR Spectrum ν (KBr) cm$^{-1}$: 3450, 2990, 1705, 1620

Elemental Analysis for $C_{24}H_{32}FN_5O_3 \cdot 2HC\lambda \cdot H_2O$: Calcd. (%): C 52.55; H 6.61; N 12.76. Found (%): C 52.30, H 6.70; N 12.61.

EXAMPLE 71

Synthesis of
2-[2-[4-(2-Fluoro-4-morpholinobenzoyl)piperidin-1-yl]ethyl]-5,6,7,8-tetrahydro-1,2,4-triazolo[4,3-a]pyridin-3(2H)-one In the manner described in Example 48, the entitled compound was obtained as pale yellow crystals from 2-[2-[(4-methylbenzenesulfonyloxy)ethyl] -5,6,7,8-tetrahydro-1,2,4-triazolo[4,3-a]pyridin-3(2H)-one and 4-(2-fluoro-4-morpholinobenzoyl)piperidine.

NMR Spectrum (CDC$\lambda_3$) δ: 1.48–2.38 (11H, m), 2.62–2.81 (4H, m), 2.94–3.13 (2H, m), 3.23–3.37 (4H, m), 3.60 (2H, t), 3.78–3.97 (6H, m), 6.36–6.72 (2H, m), 7.78 (1H, dd)

The above crystals were dissolved in methanol, and concentrated hydrochloric acid was added thereto. The mixture was concentrated to dryness under reduced pressure, and the residue was crystallized from a mixture of methanol and isopropyl ether, followed by recrystallization from a mixture of methanol and isopropyl ether to give the hydrochloride of the entitled compound as colorless crystals.

Melting Point: 242°–245° C.

NMR Spectrum (DMSO-$d_6$) δ: 1.56–2.10 (11H, m), 2.83–3.88 (16H, m), 4.10 (2H, t), 6.63–7.02 (2H, m), 7.60–7.87 (1H, m)

IR Spectrum ν (KBr) cm$^{-1}$: 3450, 2950, 2850, 2320, 1695, 1655, 1615

Elemental Analysis for $C_{24}H_{32}FN_5O_3 \cdot HC\lambda$: Calcd. (%): C 58.35; H 6.73; N 14.17. Found (%): C 58.17; H 6.90; N 14.10.

EXAMPLE 72

Synthesis of
2-[2-[4-(4-Fluorobenzoyl)-4-phenylpiperidin-1-yl]ethyl]-5,6,7,8-tetrahydro-1,2,4-triazolo[4,3-a]pyridin-3(2H)-one In the manner described in Example 52, the entitled compound was obtained as a colorless oily substance from 2-(2-chloroethyl)-5,6,7,8-tetrahydro-1,2,4-triazolo[4,3-a]pyridin-3(2H)-one and 4-(4-fluorobenzoyl)-4-phenylpiperidine.

NMR Spectrum (CDC$\lambda_3$) δ: 1.8–2.9 (16H, m), 3.59 (2H, t like), 3.85 (2H, t), 6.89 (2H, t), 7.3–7.5 (7H, m)

EXAMPLE 73

Synthesis of
2-[2-[4-(4-Fluorobenzoyl)-4-phenylpiperidin-1-yl]ethyl]-5,6,7,8-tetrahydro-1,2,4-triazolo[4,3-a]pyridin-3(2H)-one Hydrochloride Hydrate In 50 mλ of methanol was dissolved 1.28 g of 2-[2-[4-(4-fluorobenzoyl)-4-phenylpiperidin-1-yl]ethyl]-5,6,7,8-tetrahydro-1,2,4-triazolo[4,3-a]pyridin-3(2H)-one obtained in Example 72, and 0.3 mλ of concentrated hydrochloric acid was added thereto. The mixture was concentrated to dryness under reduced pressure, and the residue was crystallized from a mixture of ethanol and ethyl ether and then recrystallized from a mixture of ethanol and isopropyl ether to obtain 0.87 g of the entitled compound as colorless crystals.

Melting Point: 139°–142° C.

NMR Spectrum (DMSO-$d_6$) δ: 1.6–2.0 (4H, m), 2.3–3.7 (14H, m), 4.1 (2H, t), 7.0–7.7 (9H, m), 11.1 (1H, bs)

IR Spectrum ν (KBr) cm$^{-1}$: 3420, 1700, 1590, 1500, 1450, 1220

Elemental Analysis for $C_{26}H_{29}FN_4O_2 \cdot HC\lambda \cdot H_2O$: Calcd. (%): C 62.08; H 6.41; N 11.14. Found (%): C 62.25; H 6.80; N 10.82.

EXAMPLE 74

Synthesis of
2-[2-[4-(4-Chlorobenzoyl)piperidin-1-yl]ethyl]-5,6,7,8-tetrahydro-1,2,4-triazolo[4,3-a]pyridin-3(2H)-one In the manner described in Example 52, the entitled compound was obtained as a colorless oily substance from 2-[2-[4-(4-chlorobetyl)-5,6,7,8-tetrahydro-1,2,4-triazolo[4,3-a]pyridin-3(2H)-one and 4-(4-chlorobenzoyl)piperidine.

NMR Spectrum (DMSO-$d_6$) δ: 1.7–2.5 (10H, m), 2.5–2.8 (4H, m), 2.9–3.4 (3H, m), 3.5–3.7 (2H, m), 3.90 (2H, t), 7.48 (2H, d), 7.92 (2H, d)

EXAMPLE 75

Synthesis of
2-[2-[4-(4-Chlorobenzoyl)piperidin-1-yl]ethyl]-5,6,7,8-tetrahydro-1,2,4-triazolo[4,3-a]pyridin-3(2H)-one Hydrochloride In 100 mλ of ethanol was dissolved 3.7 g of 2-[2-[4-(4-chlorobenzoyl)piperidin-1-yl]ethyl]-5,6,7,8-tetrahydro-1,2,4-triazolo[4,3-a]pyridin-3(2H)-one obtained in Example 74, and 2 mλ of concentrated hydrochloric acid was added thereto. The mixture was concentrated to dryness under reduced pressure, and the. residue was crystallized from a mixture of ethanol and ethyl ether to obtain 3.2 g of the entitled compound as colorless crystals.

Melting Point: 245°–248° C.

NMR Spectrum (DMSO-$d_6$) δ: 1.7–2.2 (8H, m), 2.5–2.7 (4H, m), 3.2–3.8 (7H, m), 4.0–4.3 (2H, m), 7.65 (2H, d), 8.15 (2H, d)

IR Spectrum ν (KBr) cm$^{-1}$: 1707, 1683, 1584, 1410

Elemental Analysis for $C_{20}H_{25}C\lambda N_4O_2 \cdot HC\lambda$: Calcd. (%): C 56.47; H 6.16; N 13.17. Found (%): C 56.58; H 6.02; N 12.87.

REFERENCE EXAMPLE 14

Synthesis of 6,7,8,9-Tetrahydro-2H-pyrido[1,2-a]-1,3,5-triazine-2,4(3H)-dione To a solution of 1.52 g of 2-amino-3,4,5,6-tetrahydropyridine in 30 mλ of acetonitrile, 3.86 g of diphenyl imidodicarboxylate was added. After refluxing for 2 hours, the mixture was concentrated to dryness. The residue was purified by column chromatography (silica gel, eluent: methanol-chloroform) to give 1.97 g of the entitled compound as colorless crystals.

Melting Point: 185°-187° C.

NMR Spectrum (DMSO-$d_6$) δ: 1.6–1.9 (4H, m), 2.65 (2H, t), 3.64 (2H, t), 11.39 (1H, b)

IR Spectrum ν (KBr) cm$^{-1}$: 3450, 3200, 3070, 1700, 1590, 1490, 1440, 1390

Elemental Analysis for $C_7H_9N_3O_2$: Calcd. (%): C 50.30; H 5.43; N 25.14. Found (%): C 50.42; H 5.53; N 25.02.

Compounds in REFERENCE EXAMPLES of 15 to 19 were prepared in the same manner described in Reference Example 14 (shown in Table 1).

added to the solution, and an organic layer separated was concentrated to dryness under reduced pressure. The residue was crystallized from hexane to give 9.89 g of the entitled compound as colorless crystals.

Melting point: 157°-160° C.

NMR Spectrum (DMSO-$d_6$) δ: 4.0–4.2 (2H, m), 4.3–4.5 (2H, m), 7.2–7.6 (5H, m)

IR Spectrum ν (KBr) cm$^{-1}$: 3520, 3200–2800, 1730, 1670, 1600, 1480, 1420

Elemental Analysis for $C_{10}H_9NO_4$: Calcd. (%): C 57.97; H 4.38; N 6.76. Found (%): C 57.78; H 4.36; N 6.78.

REFERENCE EXAMPLE 21

Synthesis of 5-Methyl-3-phenoxycarbonyl-2-oxazolidone

The entitled compound was prepared as colorless crystals from 5-methyl-2-oxazolidone and phenyl chloroformate in the manner described in Reference Example 20.

Melting point: 116°-119° C.

NMR Spectrum (CDCl$_3$) δ: 1.53 (3H, d), 4.0 (1H, m), 4.50 (2H, m), 7.1–7.5 (5H, m)

TABLE 1

| Number of Reference Example | 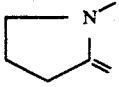 A | Melting Point (°C.) | Elemental Analysis Molecule Formula Calcd. (%): (C, H, N) Found (%): (C, H, N) | Solvent | NMR (δ) | IR ν(KBr)cm$^{-1}$ |
|---|---|---|---|---|---|---|
| 15 |  | 199–201 | $C_6H_7N_3O_2$ 47.06, 4.61, 27.44 46.90, 4.65, 27.13 | DMSO-$d_6$ | 2.87(2H, t), 2.07(2H, t), 3.82(2H, t), 11.25(1H, bs) | 3430, 3210, 3080, 1740, 1710, 1690, 1630, 1440, 1410 |
| 16 | 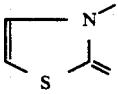 | 152–153 | $C_8H_{11}N_3O_2$ 53.03, 6.12, 23.19 53.04, 6.21, 23, 32 | CDCl$_3$ | 1.7(6H. m), 2.8(2H, m), 4.0(2H, m), 11.0(1H, bs) | 3520, 3200–2800, 1730, 1670, 1600, 1480, 1420 |
| 17 | 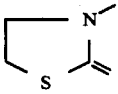 | >280 | $C_5H_3N_3O_2S$ 35.50, 1.79, 24.84 35.85, 1.95, 24, 64 | DMSO-$d_6$ | 7.12(1H, d), 7.66(1H, d), 11.67(1H, ds) | 3240, 3064, 1756, 1738, 1680, 1642, 1568, 1538, 1416 |
| 18 | 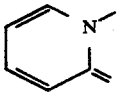 | 233–235 | $C_5H_5N_3O_2S$ 35.09, 2.94, 24.55 35.16, 2.89, 24.65 | DMSO-$d_6$ | 3.51(2H, dd), 4.22(2H, dd), 11.27(1H, bs) | 3448, 3028, 1740, 1694, 1574, 1408 |
| 19 | | >280 | $C_7H_5N_3O_2$ 51.54, 3.09, 25.76 51.44, 2.79, 25, 67 | DMSO-$d_6$ | 6.95(2H, m), 7.80(1H, ddd), 8.38(1H, d), 11.82(1H, bs) | 152, 2972, 2816, 1752, 1672, 1632, 1548 |

REFERENCE EXAMPLE 20

Synthesis of 3-Phenoxycarbonyl-2-oxazolidone

To an ice-cooled solution of 5.0 g of 2-oxazolidone and 9.08 g of phenyl chloroformate in 50 ml of dichloromethane, 6.07 g of triethylamine was added dropwise with stirring. After stirring for 20 minutes, water was IR Spectrum ν (KBr) cm$^{-1}$: 3448, 1812, 1728, 1592, 1484

Elemental Analysis for $C_{11}H_{11}NO_4$: Calcd. (%): C 59.72; H 5.01; N 6.33. Found (%): C 59.56; H 5.08; N 6.52.

REFERENCE EXAMPLE 22

Synthesis of 3-Phenoxycarbonyl-3,4,5,6-tetrahydro-2H-1,3-oxazin-2-one

A mixture of 23.8 g of bis(tri-n-butyltin)oxide and 4.8 g of 3-chloropropylisocyanate was stirred for 10 minutes at room temperature, and 15.0 g of hexamethylsulforoamide (HMPA) was added thereto. The mixture was stirred for 1 hour at 80° C. and cooled. To the mixture, 6.26 g of phenyl chloroformate was added dropwise over 5 minutes, and the mixture was stirred for 30 minutes at room temperature. After cooling, 80 ml of hexane was added to the mixture, and the resultant precipitates were collected by filtration to give 7.79 g of the entitled compound as colorless crystals.

Melting point: 94°–96° C.

NMR Spectrum (CDCl$_3$) δ: 2.19 (2H, m), 3.91 (2H, t), 4.38 (2H, t), 7.1–7.5 (5H, m)

IR Spectrum ν (KBr) cm$^{-1}$: 2924, 1808, 1788, 1696, 1480

Elemental Analysis for C$_{11}$H$_{11}$NO$_4$: Calcd. (%): C 59.72; H 5.01; N 6.33. Found (%): C 59.44; H 5.09; N 6.56.

REFERENCE EXAMPLE 23

Synthesis of 3-(2-Chloroethyl)-6,7,8,9-tetrahydro-2H-pyrido[1,2-a]-1,3,5-triazine-2,4(3H)-dione A solution of 2.79 g of diethyl azodicarboxylate in 5 ml of tetrahydrofuran was added dropwise to a solution of 2.0 g of 6,7,8,9-tetrahydro-2H-pyrido[1,2-a]-1,3,5-triazine-2,4(3H)-dione prepared in Reference Example 14, 1.13 g of 2-chloroethanol and 4.2 g of triphenylphosphine in 40 ml of tetrahydrofuran. After stirring for 1 hours, the reaction mixture was concentrated to dryness. The residue was purified by column chromatography (silica gel, eluent: methanol-chloroform) to give an oil, which was crystallized form a mixture of acetone and isopropyl ether to give 1.2 g of the entitled compound as colorless crystals.

Melting point: 61°–63° C.

NMR Spectrum (CDCl$_3$) δ: 1.8–2.2 (4H, m), 2.83 (2H, t), 3.77 (2H, t), 3.85 (2H, t), 4.28 (1H, t)

IR Spectrum ν (KBr) cm$^{-1}$: 3390, 2976, 1730, 1678, 1594, 1484

Elemental Analysis for C$_9$H$_{12}$ClN$_3$O$_2$: Calcd. (%): C 47,07; H 5.26; N 18.30. Found (%): C 47.35; H 5.49; N 18.21.

REFERENCE EXAMPLE 24

Synthesis of 3-(2-Bromoethyl)-6,7,8,9-tetrahydro-2H-pyrido[1,2-a]-1,3,5-triazine-2,4(3H)-dione The entitled compound was prepared as colorless crystals from 6,7,8,9-tetrahydro-2H-pyrido[1,2-a]-1,3,5-triazine-2,4(3H)-dione and 2-bromoethanol described in Reference Example 23.

Melting point: 64°–66° C.

NMR Spectrum (CDCl$_3$) δ: 1.8–2.1 (4H, m), 2.84 (2H, t-like), 3.59 (2H, t), 3.86 (2H, t-like), 4.33 (1H, t)

IR Spectrum ν (KBr) cm$^{-1}$: 3396, 2976, 1730, 1678, 1594, 1484

Elemental Analysis for C$_9$H$_{12}$BrN$_3$O$_2$: Calcd. (%): C 39.44; H 4.41; N 15.33. Found (%): C 39.66; H 4.48; N 15.25.

REFERENCE EXAMPLE 25

Synthesis of 3-(2-Bromoethyl)-6,7,8,9-tetrahydro-2H-pyrido[1,2-a]-1,3,5-triazine-2,4(3H)-dione (1) Phenyl N-(2-Bromoethyl)carbamate To an ice-cooled suspension of 5.0 g of 2-bromoethylamine hydrobromide and 3.91 g of phenyl chloroformate in 50 ml of dichloromethane, 5.1 g of triethylamine was added. The mixture was stirred for 2 hours, and water was added thereto. The organic phase separated was concentrated to dryness under reduced pressure. The residue was crystallized with hexane to give 5.33 g of the entitled compound as colorless crystals.

Melting point: 57°–60° C.

NMR (CDCl$_3$) δ: 3.4 (4H, m), 5.6 (1H, b), 7.0–7.5 (5H, m)

(2) 3-(2-Bromoethyl)-6,7,8,9-tetrahydro-2H-pyrido[1,2-a]-1,3,5-triazine-2,4(3H)-dione To an ice-cooled suspension of 2.44 g of phenyl N-(2-bromoethyl)carbamate and 1.64 g of phenyl chloroformate in 25 ml of acetonitrile, 1.2 g of triethylamine was added dropwise. After stirring for 20 minutes at the same temperature, the mixture was stirred for 3 hours at room temperature. The reaction mixture was concentrated to dryness under reduced pressure, and the residue was extracted with chloroform. After concentration of the chloroform solution, the residue was dissolved in 20 ml of acetonitrile, and a mixture of 1.35 g of 2-amino-3,4,5,6-tetrahydropyridine hydrochloride and 2.02 g of triethylamine was added to the solution. After stirring for 45 minutes at 60° C., the mixture was concentrated and extracted with chloroform. The solvent was evaporated, and the residue was purified by column chromatography (silica gel, eluent: methanol-chloroform). After concentration of the eluate, the residue was crystallized from a mixture of acetone and isopropyl ether to give 0.65 g of the entitled compound as colorless crystals.

Melting point: 64°–66° C.

NMR Spectrum (CDCl$_3$) δ: 1.8–2.1 (4H, m), 2.84 (2H, t-like), 3.59 (2H, t), 3.86 (2H, t-like), 4.33 (2H, t)

REFERENCE EXAMPLE 26

Synthesis of 3-(2-Bromoethyl)-6,7,8,9-tetrahydro-2H-pyrido[1,2-a]-1,3,5-triazine-2,4(3H)-dione To a mixture of 2.57 g of diphenyl imidodicarboxylate, 1.50 g of 2-bromoethanol and 3.41 g of triphenylphosphine in 30 ml of tetrahydrofuran, 2.26 g of diethyl azodicarboxylate was added dropwise with stirring. After stirring for 2 hours, 0.98 g of 2-amino-3,4,5,6-tetrahydropyridine was added, and the mixture was stirred for 2 hours at room temperature. The reaction mixture was concentrated to dryness under reduced pressure, and the residue was purified by column chromatography (silica gel, eluent: ethyl acetate). After concentration of the eluate, the residue was crystallized from a mixture of acetone and isopropyl ether to give the entitled compound as colorless crystals.

Melting point: 64°–66° C.

NMR Spectrum (CDCl$_3$) δ: 1.8–2.1 (4H, m), 2.84 (2H, t-like), 3.59 (2H, t), 3.86 (2H, t-like), 4.33 (1H, t)

IR Spectrum ν (KBr) cm⁻¹: 3396, 2976, 1730, 1678, 1594, 1484

Elemental Analysis for $C_9H_{12}BrN_3O_2$: Calcd. (%): C 39.44; H 4.41; N 15.33. Found (%): C 39.58; H 4.62; N 15.13.

REFERENCE EXAMPLE 27

Synthesis of 3-(2-Hydroxyethyl)-6,7,8,9-tetrahydro-2H-pyrido[1,2-a]-1,3,5-triazine-2,4(3H)-dione To an ice-cooled solution prepared from 0.46 g of sodium and 20 ml of anhydrous ethanol, 2.69 g of 2-amino-3,4,5,6-tetrahydropyridine hydrochloride was added. After stirring for 40 minutes at room temperature, the insoluble material was filtered off, and the filtrate was concentrated, to dryness. The residue was dissolved in 30 ml of acetonitrile, and 4.14 g of 3-phenoxycarbonyl-2-oxazolidone was added thereto. The mixture was stirred for 1.5 hours at 60° C. After concentration of the reaction mixture, the residue was purified by column chromatography (silica gel, eluent: methanol-chloroform) to give 3.45 g of the entitled compound as colorless crystals.

Melting point: 125°–128° C.

NMR Spectrum (DMSO-$d_6$) δ: 1.8–2.1 (4H, m), 2.69 (1H, s), 2.82 (2H, t), 3.86 (4H, t-like), 4.14 (2H, t)

IR Spectrum ν (KBr) cm⁻¹: 3293, 2960, 1730, 1684, 1602, 1504, 1452, 1416

Elemental Analysis for $C_9H_{13}N_3O_3$: Calcd. (%): C 51.18; H 6.20; N 19.89. Found (%): C 50.83; H 6.43; N 19.64.

Compounds in Reference Example 28 to 31 were prepared in the same manner described in Reference Example 27 (shown in Table 2).

REFERENCE EXAMPLE 32

Synthesis of 3-(1-Hydroxypropan-2-yl)-6,7,8,9-tetrahydro-2H-pyrido[1,2-a]-1,3,5-triazine-2,4(3H)-dione The entitled compound was prepared as colorless crystals from 5-methyl-3-phenoxycarbonyl-2-oxazolidone prepared in Reference Example 21 and 2-amino-3,4,5,6-tetrahydropyridine hydrochloride in the same manner described in Reference Example 27.

Melting point: 109°–112° C.

NMR Spectrum (DMSO-$d_6$) δ: 1.4 (3H, d), 1.7–2.1 (4H, m), 2.80 (2H, t), 3.34 (1H, s), 3.6–3.9 (3H, m), 4.09 (1H, dd), 5.02 (1H, m)

IR Spectrum ν (KBr) cm⁻¹: 3300, 2948, 2884, 1680, 1606, 1490

Elemental Analysis for $C_{10}H_{15}N_3O_3$: Calcd. (%): C 53.32; H 6.71; N 18.65. Found (%): C 53.26; H 6.89; N 18.82.

REFERENCE EXAMPLE 33

Synthesis of 3-(2-Methanesulfonyloxyethyl)-6,7,8,9-tetrahydro-2H-pyrido[1,2-a]-1,3,5-triazine-2,4(3H)-dione To an ice-cooled solution of 1.80 g of 3-(2-hydroxyethyl)-6,7,8,9-tetrahydro-2H-pyrido[1,2-a]-1,3,5-triazine-2,4(3H)-dione prepared in Reference Example 27 and 1.20 g of triethylamine in 25 ml of acetonitrile, 1.17 g of methanesufonyl chloride was added dropwise. After stirring for 30 minutes, the mixture was concentrated to dryness, and the residue was extracted with chloroform. Concentration of the chloroform solution gave 2.34 g of the entitled compound as an yellow oil.

NMR Spectrum (CDCl₃) δ: 1.8–2.1 (4H, m), 2.8 (2H, t), 3.1 (3H, s), 3.9 (2H, t), 4.3 (2H, t), 4.5 (2H, t)

TABLE 2

| Number of Reference Example | A (ring) | n | Melting Point (°C.) | Elemental Analysis Molecule Formula Calcd. (%): (C, H, N) Found (%): (C, H, N) | Solvent | NMR (δ) | IR ν(KBr)cm⁻¹ |
|---|---|---|---|---|---|---|---|
| 28 | pyrrolidine-N | 2 | 119–121 | $C_8H_{11}N_3O_3$<br>48.73, 5.62, 21.31<br>48.64, 5.64, 21.18 | DMSO-$d_6$ | 2.09(2H, m), 2.90(2H, t), 3.50(2H, q), 3.7–4.0(4H, m) | 3328, 2960, 1720, 1692, 1642, 1484, 1450 |
| 29 | azepane-N | 2 | 130–133 | $C_{10}H_{15}N_3O_3$<br>53.32, 6.71, 19.65<br>52.96, 6.66, 19.38 | CDCl₃ | 1.6–2.0(6H, m), 2.9(2H, m), 3.85(2H, t), 4.13(4H, t-like) | 3340, 2944, 1726, 1680, 1596, 1476 |
| 30 | thiazolidine-N | 2 | 102–105 | $C_7H_9N_3O_3S$<br>39.07, 4.21, 19.52<br>38.80, 4.05, 19.28 | DMSO-$d_6$ | 3.4–3.6(4H, m), 3.78(2H, t), 4.23(2H, t), 4.70(1H, t) | 3324, 1734, 1674, 1574, 1452, 1432 |
| 31 | piperidine-N | 3 | 136–138 | $C_{10}H_{15}N_3O_3$<br>53.32, 6.71, 18.65<br>53.31, 6.72, 18.68 | DMSO-$d_6$ | 1.6–2.0(6H, m), 2, 66(2H, t-like), 3.43(2H, q), 3.6–4.0(4H, m), | 3312, 1730, 1674, 1592, 1490 |

REFERENCE EXAMPLE 34

Synthesis of 3-[2-(4-Methylbenzenesulfonyloxy)ethyl]-6,7,8,9-tetrahydro-2H-pyrido[1,2-a]-1,3,5-triazine-2,4(3H)-dione The entitled compound was prepared as a yellowish solid from 3-(2-hydroxyethyl)-6,7,8,9-tetrahydro-2H-pyrido[1,2-a]-1,3,5-triazine-2,4(3H)-dione prepared in Reference Example 27 and 4-methylbenzenesulfonyl chloride in the manner described in Reference Example 33.

NMR Spectrum (CDCl$_3$) δ: 1.8-2.1 (4H, m), 2.44 (3H, s), 2.81 (2H, t-like), 3.83 (3H, t-like), 4.3 (4H, m), 7.32 (2H, d), 7.77 (2H, dd)

EXAMPLE 76

Synthesis of 3-[2-[4-(4-Fluorobenzoyl)-piperidin-1-yl)ethyl]-6,7,8,9-tetrahydro-2H-pyrido[1,2-a]-1,3,5-triazine-2,4(3H)-dione A solution of 3.3 g of 3-(2-methanesulfonyloxyethyl)-6,7,8,9-tetrahydro-2H-pyrido[1,2-a]-1,3,5-triazine-2,4(3H)-dione prepared in Reference Example 33, 1.01 g of triethylamine and 2.27 g of 4-(4-fluorobenzoyl)piperidine in 25 ml of acetonitrile was refluxed for 4 hours. After concentration of the reaction mixture, the residue was extracted with chloroform. The chloroform solution was concentrated to dryness, and the residue was purified by column chromatography (silica gel, eluent: methanol-chloroform) to give 2.17 g of the entitled compound as yellow crystals.

Melting point: 170°-172° C.

NMR Spectrum (CDCl$_3$) δ: 1.8-2.2 (10H, m), 2.26 (2H, t), 2.81 (2H, t), 3.0-3.3 (3H, m), 3.84 (2H, t), 4.06 (2H, t), 7.13 (2H, t), 7.95 (2H, dd)

IR Spectrum ν (KBr) cm$^{-1}$: 1730, 1670, 1600, 1490, 1450, 1410

Elemental Analysis for C$_{21}$H$_{25}$FN$_4$O$_3$: Calcd. (%): C 62.99; H 6.29; N 13.99. Found (%): C 62.76; H 6.32; N 14.05.

EXAMPLE 77

Synthesis of 3-[2-[4-[Bis(4-fluorophenyl)-methylene]piperidin-1-yl]ethyl]-6,7,8,9-tetrahydro-2H-pyrido1,2-a]-1,3,5-triazine-2,4(3H)-dione The entitled compound was prepared as a yellowish oil from 3-(2-methanesulfonyloxyethyl)-6,7,8,9-tetrahydro-2H-pyrido[1,2-a]-1,3,5-triazine-2,4(3H)-dione prepared in Reference Example 33 and 4-[bis(4-fluorophenyl)methylene]-piperidine in the manner described in Example 76.

NMR Spectrum (CDCl$_3$) δ: 1.8-2.0 (4H, m), 2.3 (4H, m) 2.5-2.8 (8H, m), 3.8 (2H, t), 4.07 (2H, t), 6.96 (4H, d), 7.04 (4H, s)

TEST EXAMPLE 1

Antagonistic Activity on Serotonin 2-Receptor

A test compound dissolved in purified water was orally administered to an SD-SLC male rat at a dose of 10 mg/kg. After 30 minutes from the administration, the rat was anesthetized with urethane (1 g/kg, i.p.) and α-Chloralose (80 mg/kg, i.p.). A polyethylene cannula was inserted into the carotid artery, and the blood pressure was recorded on a polygraph by using a pressure transducer. After 60 minutes or 180 minutes from the administration of the test compound, 300 μg/kg of serotonin was intravenously injected, and an increase in blood pressure was observed. Serotonin 2 (hereinafter referred to as 5-HT$_2$) antagonistic activity of the test compound was calculated as a percentage of inhibition of an increase in blood pressure induced by 5-HT$_2$. The inhibitory effect of the test compound wa compared with that of vehicle solution treated group. The results obtained are shown in Table 3 below.

TEST EXAMPLE 2

Antagonistic Activity on Sympathetic Nerve α$_1$-Receptor

A test compound dissolved in purified water was orally administered to an SD-SLC male rat at a dose of 10 mg/kg. After 30 minutes from the administration, the rat was anesthetized with urethane (1 g/kg, i.p.) and α-Chloralose (80 mg/kg, i.p.). A polyethylene cannula was inserted into the carotid artery, and the blood pressure was recorded on a polygraph by using a pressure transducer. After 60 minutes from the administration of the test compound, 100 μg/kg of phenylephrine was intravenously injected to observe an increase in blood pressure. Sympathetic nerve α$_1$-receptor antagonistic activity of the test compound was calculated as a percentage of inhibition of an increase in blood pressure induced by phenylephrine. The inhibitory effect of the test compound was compared with that of vehicle solution treated group. The results obtained are shown in Table 3.

TEST EXAMPLE 3

Toxicity in Mice

A test compound dissolved or suspended in a 1% methyl cellulose solution was orally administered to ddy male mice (4 or 5 mice per group) at a dose of 200 mg/kg once a day for consecutive 4 days. The number of dead animals per group was counted on the day next to the final administration day. As a control, 10 mλ/kg of 1% methyl cellulose solution was orally administered. The results obtained are shown in Table 3.

TABLE 3

| Test Compound | Antagonistic Activity 5-HT$_2$ (%) | Antagonistic Activity α$_1$ (%) | Toxicity (Death Rate) |
|---|---|---|---|
| Compound of Example 2 | 93* | 9* | 1/5 |
| Compound of Example 3 | 93* | 39* | 0/5 |
| Compound of Example 11 | 83* | 0* | |
| Compound of Example 18 | 93* | 6* | 0/5 |
| Compound of Example 20 | 83* | 1* | |
| Compound of Example 21 | 93* | 3* | |
| Compound of Example 34 | 90* | 3* | 1/4 |
| Compound of Example 36 | 84* | 3* | 0/5 |
| Compound of Example 44 | 89* | 2* | 2/5 |
| Compound of Example 49 | 82** | 3** | 0/5 |
| Compound of Example 51 | 95* | 3* | 0/5 |
| Compound of Example 63 | 85* | 0* | |
| Compound of Example 67 | 90* | 4* | |

TABLE 3-continued

| Test Compound | Antagonistic Activity | | Toxicity (Death Rate) |
|---|---|---|---|
| | 5-HT$_2$ (%) | α$_1$ (%) | |
| Compound of Example 75 | 83* | 17* | 0/3 |
| Ketanserin | 96* | 73* | 5/5 |
| Ritanserin | 84* | 5* | 3/5 |

Note:
*After 60 minutes from the administration
**After 180 minutes from the administration

TEST EXAMPLE 4

Binding Activity to Serotonin 2-Receptor

A male SD rat was decapitated under anesthesia, and the frontal cortex was removed to obtain a membrane preparation. $^3$H-Ketanserin and Methysergide were used as a labelled ligand and a non-specific binding reagent, respectively. These reagents and a test compound thereof were dissolved in a 5% methanol tris-buffer solution. After incubation, this solution was filtered by suction through a GF/B glass filter. Radioactivity of $^3$H-Ketanserin collected on the filter was measured with a liquid scintillation counter. A Scatchard plot was prepared from the resulting radioactivity values, and a dissociation constant of serotonin 2-receptor and a receptor density of the membrane preparation were obtained. Further, from the receptor-binding inhibition curve of the compound is obtained a 50% inhibitory concentration, and a dissociation constant indicative of the binding affinity to serotonin 2-receptor was calculated. As a result, the dissociation constant of a hydrochloride of 3-[2-[4-(fluorobenzoyl)piperidin-1-yl]ethyl]-6,7,8,9-tetrahydro-2H-pyrido[1,2-a]-1,3,5-triazine-2,4(3H)-dione (hereinafter referred to as compound A) was found to have a dissociation constant of 15 nM for serotonin 2-receptor.

TEST EXAMPLE 5

Effect in Acute Cardiac Infarction Model Experimental Preparation

Mongrel dogs (body weight: 8 to 20 kg) under anesthesia were ventilated artificially and underwent a left thracotomy. A needle type platinum electrode was placed in the myocardium nourished by the left anterior descending coronary artery (hereinafter referred to as LDA) to a depth of about 1 cm, and the blood flow in the myocardial tissue was determined by a hydrogen gas clearance method. A polyethylene cannula was inserted into the femoral artery, and the blood pressure and heart rate were recorded A cannula was inserted into the femoral artery for administration of a drug and also into the carotid artery from which a blood sample was to be taken. After stabilization period of the test preparation, LDA was ligated with a clamp. After 2 hours from the ligature, the clamp was released for reperfusion. After observation for the following 4 hours, the heart was excised. A 1% triphenyltetrazolium chloride solution was infused from the left coronary anterior descending branch, while retrogressively infusing a 0.5% Evans' Blue solution from the aorta, each at a pressure of about 80 mmHg, and they were perfused through the heart for 15 minutes for double staining. Then, the heart was washed and sliced at 1 cm intervals from the apex in the direction vertical to the longer axis. Each slice at the left ventricle was divided into a part which was in risk of cardiac infarction indicated by Evans' Blue stain (hereinafter referred to as risk area) and a normal area, and each area was weighed. The weight of the left ventricle (the sum of the risk area and the normal area) and that of the risk area of each slice were individually added up to obtain the weight of the whole left ventricle and the total weight of the risk area. Further, of each slice, the area of the risk area which was not stained with Evans' Blue and that of a cardiac infarction area within the risk area which remained white, i.e., which was stained neither in blue with Evans' Blue nor in red with triphenyltetrazolium chloride, were measured to obtain a ratio of cardiac infarction part to the whole left ventricle (infarction size).

Administration of Drug

A hydrochloride of compound A or physiological saline was infused by an intravenous drip at a rate of 1 mλ/kg/hr from 20 minutes before the ligature of the left coronary anterior descending branch through the end of the experiment. The dose of Compound A hydrochloride was 1 mg/kg/hr. The experiment was conducted for the following groups.

1) Control Group (11 cases): treated with saline
2) Test Group (12 cases): treated with hydrochloride of compound A Test Result The results obtained are shown in Table 4.

TABLE 4

| | Control Group | Test Group |
|---|---|---|
| Myocardial Blood Flow (ml/min/100 g) | 62 ± 9 | 89 ± 14* |
| Infarction Size: | | |
| Left Ventricle Weight (g) | 68 ± 5 | 65 ± 5 |
| Dangerous part Weight (g) | 21 ± 3 | 19 ± 2 |
| Infarction Size (%) | 30 ± 7 | 11 ± 3* |
| Blood Pressure (mmHg) | 118 ± 4 | 103 ± 4* |
| Heart Rate (beats/min) | 158 ± 8 | 150 ± 9 |

Note: The values indicate mean ± S.E.M.
*P < 0.05

As is apparent from the results in Table 4, after the ligature at LDA, reperfusion of blood restored the myocardial blood flow to only 60% of the initial value before the ligature in the control group, whereas in the test group the once deteriorated myocardial blood flow was restored to a level significantly higher than that of the control group. Since there was no substantial difference between the two groups in the left ventricle weight and the risk area weight, the degree of injure given to each heart was considered equal. Under these conditions, compound A significantly reduced the myocardial infarction size. It wa thus proved that compound A acts to improve microcirculatory disturbances accompanied by ischemia, preventing the myocardium from necrotizing changes. It was also confirmed that compound A has only a slight influence on blood pressure.

Accordingly, compound A was proved useful for prevention and treatment of ischemic heart diseases.

TEST EXAMPLE 6

Effect in Angina Pectoris Model Experimental Preparation

Mongrel dogs (body weight: 8 to 20 kg) under anesthesia with pentobarbital (30 mg/kg, i.v.) were ventilated artificially and underwent a left thoracotomy. LDA was separated from connected tissues. A silicone tube for partial occlusion was placed around the LDA, and a probe for blood flow rate measurement was fixed in the neighborhood. The blood flow rate was measured with a pulse Doppler blood flow meter. A cannula was inserted into a branch distal to the occlusion site of the left coronary artery, and the coronary blood pressure was measured. A polyethylene cannula was inserted into the femoral artery, and the systemic blood pressure and heart rate were recorded. A cannula was inserted to the femoral vein for administration of a drug. After stabilization of the preparation, LDA was partially occluded so as to reduce the blood flow rate by 20% to induce an angina pectoris-like condition in which the blood flow rate of LDA is cyclically reduced.

Administration of Drug

One hour after the above-described angina pectoris-like condition was presented, a maleate of compound A was administered into the femoral vein at a dose of 0.1 mg/kg. Then, the cyclic coronary flow reduction was disappeared. The effect of the drug was expressed in terms of frequency of the periodic reduction of blood flow rate. The maleate of compound A was used as dissolved in physiological saline.

Test Results

The results obtained are shown in Table 5 below.

TABLE 5

| Dose of Compound A | Frequency of Periodic Reduction in Blood Flow Rate | |
| --- | --- | --- |
| | Before Admin. | After Admin. |
| 0.1 mg/kg, i.v. | 9.9 ± 2.5 | 2.3 ± 1.2** |

Note: Values are means ± S.E.M.
**P < 0.01 (compared with the value before administration)

It can be seen from Table 3 that compound A, administered at a low dose, significantly reduces the frequency of the cyclic coronary flow reduction as compared with that before administration. Compound A was thus proved effective to suppress anginal attacks.

TEST EXAMPLE 7

Toxicity in Rats

Toxicity of the maleate of compound A in rats in oral administration for 10 days is shown in Table 6.

TABLE 6

| Dose | Number of Test Animals | Number of Dead Animals |
| --- | --- | --- |
| 50 mg/kg (p.o.) | 5 | 0 |
| 200 mg/kg (p.o.) | 5 | 0 |
| 800 mg/kg (p.o.) | 5 | 0 |

While the invention has been described in detail and with reference to specific embodiments thereof, it will be apparent to one skilled in the art that various changes and modifications can be made therein without departing from the spirit and scope thereof.

What is claimed is:

1. A heterocyclic compound represented by formula (I):

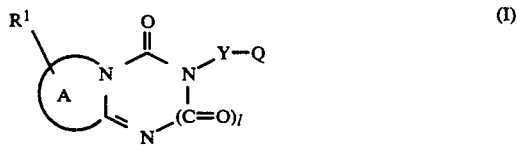

wherein $R^1$ represents a hydrogen atom, an alkyl group, an aryl group which may be substituted with one or more substituents selected from the group consisting of a halogen atom, an alkoxy group, an alkyl group and a trihalogenomethyl group; $\lambda$ represents 1; ring A represents a 6-membered heterocyclic ring containing the nitrogen atom shared with the triazine ring, and which may contain on or more double bonds; Y represents a substituted or unsubstituted alkylene group having from 1 to 15 carbon atoms; and Q represents a group represented by formula (II):

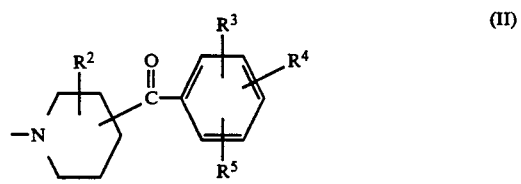

wherein $R^2$ represents a hydrogen atom, a hydroxyl group, an alkyl group or an aryl group which may be substituted with one or more substituents selected from the group consisting of a halogen atom, a hydroxyl group, an alkyl group, an alkoxy group and a trihalogenomethyl group; and $R^3$, $R^4$ and $R^5$, which may be the same or different, each represents a hydrogen atom, a halogen atom, an alkyl group, an alkoxy group, an alicyclic heterocyclic group or a trihalogenomethyl group, or a group represented by formula (III):

wherein $Ar^1$ and $Ar^2$, which may be the same or different, each represents an aryl group or an aromatic heterocyclic group, each of which may be substituted with one to three substituents selected from the group consisting of a halogen atom, a hydroxyl group, an alkoxy group, an alkyl group and a trihalogenomethyl group or salts thereof.

2. A heterocyclic compound or salt thereof as claimed in claim 1, wherein Y is an alkylene group having from 2 to 7 carbon atoms.

3. A heterocyclic compound or salt thereof as claimed in claim 1, wherein Y is a group of the formula:

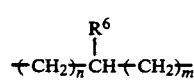

wherein $R^6$ represents a hydrogen atom, an alkyl group, an aryl group which may be substituted with one or more substituents selected from the group consisting of a halogen atom, an alkoxy group, an alkyl group and a trihalogenomethyl group; and n and m each represents 0 or an integer of from 1 to 6.

4. A heterocyclic compound or salt thereof as claimed in claim 1, wherein Q is represented by formula:

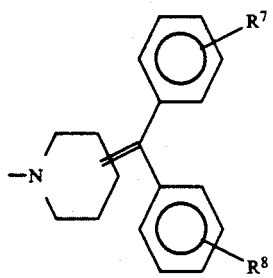

wherein $R^7$ and $R^8$, which may be the same or different represents a hydrogen atom, a hydroxyl group, an alkyl group, an alkoxy group, a halogen atom or a trihalogenomethyl group.

5. A heterocyclic compound or salt thereof as claimed in claim 1, wherein Q is represented by formula:

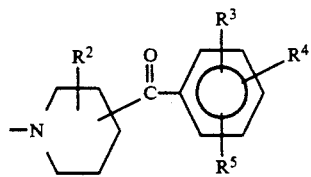

wherein $R^2$ represents a hydrogen atom, a hydroxyl group, an alkyl group, an aryl group which may be substituted with one or more substituents selected from the group consisting of an alkyl group, an alkoxy group, a halogen atom, and a trihalogenomethyl group; and $R^3$, $R^4$ and $R^5$, which may be the same or different, each represents a hydrogen atom, an alkyl group, an alkoxy group, a halogen atom, or an alicyclic heterocyclic group.

6. A heterocyclic compound or salt thereof as claimed in claim 1, wherein ring A is a piperidine, Y is an alkylene group having 1 to 6 carbon atoms and Q is a group represented by formula (II′) or (III′)

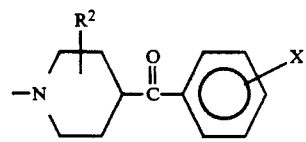

or

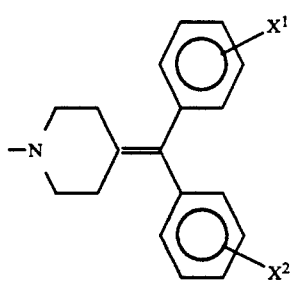

wherein $R^{21}$ represents a hydrogen atom or a hydroxyl group; X represents a halogen atom; and $X^1$ and $X^2$, which may be the same or different, each represents a halogen atom.

7. 3-[2-[4-(4-fluorobenzoyl)piperidin-1-yl]ethyl-6,7,8,9-tetrahydro-2H-pyrido[1,2-a]-1,3,5-triazine-2,4(3H)-dione or an acid addition salt thereof according to claim 1.

8. A serotonin 2-receptor antagonist composition which comprises a heterocyclic compound represented by formula (I):

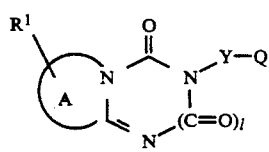

wherein $R^1$ represents a hydrogen atom, an alkyl group, an aryl group which may be substituted with one or more substituents selected from the group consisting of a halogen atom, an alkoxy group, an alkyl group and a trihalogenomethyl group; λ represents 1; ring A represents a 6-membered heterocyclic ring containing the nitrogen atom shared with the triazine ring, and which may contain one or more double bonds; Y represents a substituted or unsubstituted alkylene group having 1 to 15 carbon atoms; and Q represents a group represented by formula (II):

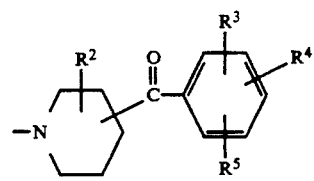

wherein $R^2$ represents a hydrogen atom, a hydroxyl group, an alkyl group, an aryl group which may be substituted with one or more substituents selected from the group consisting of a halogen atom, a hydroxyl group, an alkyl group, an alkoxy group, and a trihalogenomethyl group; and $R^3$, $R^4$ and $R^5$, which may be the same or different, each represents a hydrogen atom, a halogen atom, an alkyl group, an alkoxy group, an alicyclic heterocyclic group or a trihalogenomethyl group, or a group represented by formula (III):

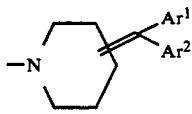 (III)

wherein Ar¹ and Ar², which may be the same or different, each represents an aryl group or an aromatic heterocyclic group, each of which may be substituted with one to three substituents selected from the group consisting of a halogen atom, a hydroxyl group, an alkoxy group, an alkyl group and a trihalogenomethyl group, or salt thereof as an active ingredient and a pharmaceutically acceptable carrier.

9. A method of treating heart disease which comprises administering a therapeutically effective amount of a heterocyclic compound represented by formula (I):

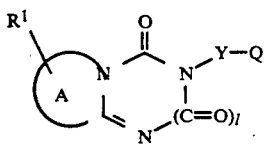 (I)

wherein R¹ represents a hydrogen atom, an alkyl group, an aryl group which may be substituted with one or more substituents selected from the group consisting of a halogen atom, an alkoxy group, an alkyl group and a trihalogenomethyl group; λ represents 1; ring A represents a 6-membered heterocyclic ring containing the nitrogen atom shared with the triazine ring, and which may contain one or more double bonds; Y represents a substituted or unsubstituted alkylene group having from 1 to 15 carbon atoms; and Q represents a group represented by formula (II):

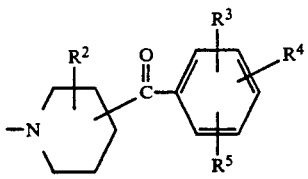 (II)

wherein R² represents a hydrogen atom, a hydroxyl group, an alkyl group or an aryl group which may be substituted with one or more substituents selected from the group consisting of a halogen atom, a hydroxyl group, an alkyl group, an alkoxy group and a trihalogenomethyl group; and R³, R⁴ and R⁵, which may be the same or different, each represents a hydrogen atom, a halogen atom, an alkyl group, an alkoxy group, an alicyclic heterocyclic group or a trihalogenomethyl group, or a group represented by formula (III):

 (III)

wherein Ar¹ and Ar², which may be the same or different, each represents an aryl group or an aromatic heterocyclic group, each of which may be substituted with one to three substituents selected from the group consisting of a halogen atom, a hydroxyl group, an alkoxy group, an alkyl group and a trihalogenomethyl group, or salt thereof to a subject so afflicted.

* * * * *